(12) United States Patent
Wham et al.

(10) Patent No.: US 9,375,270 B2
(45) Date of Patent: *Jun. 28, 2016

(54) VESSEL SEALING SYSTEM

(71) Applicant: COVIDIEN AG, Neuhausen Am Rheinfall (CH)

(72) Inventors: Robert H. Wham, Boulder, CO (US); Steven P. Buysse, Niwot, CO (US); James H. Orszulak, Nederland, CO (US)

(73) Assignee: COVIDIEN AG, Neuhausen Am (CH)

( * ) Notice: Subject to any disclaimer, the term of this patent is extended or adjusted under 35 U.S.C. 154(b) by 315 days.

This patent is subject to a terminal disclaimer.

(21) Appl. No.: 14/072,312

(22) Filed: Nov. 5, 2013

(65) Prior Publication Data

US 2014/0058381 A1 Feb. 27, 2014

Related U.S. Application Data

(63) Continuation of application No. 13/652,932, filed on Oct. 16, 2012, now Pat. No. 8,591,506, which is a continuation of application No. 12/057,557, filed on Mar. 28, 2008, now Pat. No. 8,287,528, which is a (Continued)

(51) Int. Cl.
*A61B 18/14* (2006.01)
*A61B 18/18* (2006.01)

(Continued)

(52) U.S. Cl.
CPC .................. *A61B 18/18* (2013.01); *A61B 18/00* (2013.01); *A61B 18/1206* (2013.01); *A61B 18/1442* (2013.01); *A61B 18/1445* (2013.01); *A61B 18/1482* (2013.01); *A61B 17/12* (2013.01); *A61B 2017/2945* (2013.01); *A61B 2018/0063* (2013.01); *A61B 2018/00404* (2013.01);

(Continued)

(58) Field of Classification Search
CPC ........... A61B 18/1442; A61B 18/1445; A61B 18/1206; A61B 2018/1455; A61B 2018/00601; A61B 2018/00607; A61B 2018/1412; A61B 2018/1467

See application file for complete search history.

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| CA | 2 104 423 | 2/1994 |
| CA | 2 520 413 | 3/2007 |

(Continued)

OTHER PUBLICATIONS

U.S. Appl. No. 08/926,869, filed Sep. 10, 1997, Chandler.

(Continued)

*Primary Examiner* — Michael Peffley

(57) ABSTRACT

An electrosurgical system is disclosed. The electrosurgical system includes an electrosurgical generator adapted to supply electrosurgical energy to tissue. The electrosurgical generator includes impedance sensing circuitry which measures impedance of tissue, a microprocessor configured to determine whether a tissue reaction has occurred as a function of a minimum impedance value and a predetermined rise in impedance, wherein tissue reaction corresponds to a boiling point of tissue fluid, and an electrosurgical instrument including at least one active electrode adapted to apply electrosurgical energy to tissue.

9 Claims, 17 Drawing Sheets

Related U.S. Application Data continuation of application No. 10/626,390, filed on Jul. 24, 2003, now Pat. No. 7,364,577, which is a continuation-in-part of application No. 10/073,761, filed on Feb. 11, 2002, now Pat. No. 6,796,981, which is a continuation-in-part of application No. 09/408,944, filed on Sep. 30, 1999, now Pat. No. 6,398,779.

(60) Provisional application No. 60/105,417, filed on Oct. 23, 1998.

(51) Int. Cl.
*A61B 18/12* (2006.01)
*A61B 17/12* (2006.01)
*A61B 17/29* (2006.01)
*A61B 18/00* (2006.01)

(52) U.S. Cl.
CPC ............... *A61B2018/00601* (2013.01); *A61B 2018/00684* (2013.01); *A61B 2018/00702* (2013.01); *A61B 2018/00726* (2013.01); *A61B 2018/00791* (2013.01); *A61B 2018/00827* (2013.01); *A61B 2018/00875* (2013.01); *A61B 2018/1432* (2013.01)

(56) References Cited

U.S. PATENT DOCUMENTS

| | | |
|---|---|---|
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 1,908,201 A | 5/1933 | Welch et al. |
| 1,918,889 A | 7/1933 | Bacon |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,113,246 A | 5/1937 | Wappler |
| 2,141,936 A | 12/1938 | Schmitt |
| 2,176,479 A | 10/1939 | Willis |
| 2,245,030 A | 4/1941 | Gottesfeld et al. |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 2,824,915 A | 2/1958 | Buturuga |
| 3,073,311 A | 1/1963 | Tibbs et al. |
| 3,100,489 A | 8/1963 | Bagley |
| 3,204,807 A | 9/1965 | Ramsing |
| 3,372,288 A | 3/1968 | Wigington |
| 3,459,187 A | 8/1969 | Pallotta |
| 3,561,448 A | 2/1971 | Peternel |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,798,688 A | 3/1974 | Wasson |
| 3,801,766 A | 4/1974 | Morrison, Jr. |
| 3,839,614 A | 10/1974 | Saganowski et al. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,031,898 A | 6/1977 | Hiltebrandt et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,102,471 A | 7/1978 | Lore et al. |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,200,105 A | 4/1980 | Gonser |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,306,561 A | 12/1981 | De Medinaceli |
| 4,311,145 A | 1/1982 | Esty et al. |
| D263,020 S | 2/1982 | Rau, III |
| 4,315,510 A | 2/1982 | Kihn |
| 4,363,944 A | 12/1982 | Poirier |
| 4,370,980 A | 2/1983 | Lottick |
| 4,375,218 A | 3/1983 | DiGeronimo |
| 4,394,552 A | 7/1983 | Schlosser |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,513,271 A | 4/1985 | Reisem |
| 4,535,773 A | 8/1985 | Yoon |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,625,723 A | 12/1986 | Altnether et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,753,235 A | 6/1988 | Hasson |
| 4,754,892 A | 7/1988 | Retief |
| 4,763,669 A | 8/1988 | Jaeger |
| D298,353 S | 11/1988 | Manno |
| 4,781,175 A | 11/1988 | McGreevy et al. |
| D299,413 S | 1/1989 | DeCarolis |
| 4,805,616 A | 2/1989 | Pao |
| 4,827,927 A | 5/1989 | Newton |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,890,610 A | 1/1990 | Kirwan, Sr. et al. |
| 4,938,761 A | 7/1990 | Ensslin |
| 4,947,009 A | 8/1990 | Osika et al. |

(56) References Cited

U.S. PATENT DOCUMENTS

| | | |
|---|---|---|
| 4,973,801 A | 11/1990 | Frick et al. |
| 4,985,030 A | 1/1991 | Melzer et al. |
| 5,007,908 A | 4/1991 | Rydell |
| 5,019,678 A | 5/1991 | Templeton et al. |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,052,402 A | 10/1991 | Bencini et al. |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,144,323 A | 9/1992 | Yonkers |
| 5,147,357 A | 9/1992 | Rose et al. |
| 5,151,102 A | 9/1992 | Kamiyama et al. |
| 5,151,978 A | 9/1992 | Bronikowski et al. |
| 5,158,561 A | 10/1992 | Rydell et al. |
| 5,169,396 A | 12/1992 | Dowlatshahi et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,231,997 A | 8/1993 | Kikuchi et al. |
| 5,244,462 A | 9/1993 | Delahuerga et al. |
| 5,250,047 A | 10/1993 | Rydell |
| 5,250,056 A | 10/1993 | Hasson |
| 5,250,063 A | 10/1993 | Abidin et al. |
| 5,254,129 A | 10/1993 | Alexander |
| 5,258,001 A | 11/1993 | Corman |
| 5,258,006 A | 11/1993 | Rydell et al. |
| 5,261,918 A | 11/1993 | Phillips et al. |
| 5,267,998 A | 12/1993 | Hagen |
| 5,269,780 A | 12/1993 | Roos |
| 5,269,804 A | 12/1993 | Bales et al. |
| D343,453 S | 1/1994 | Noda |
| 5,275,615 A | 1/1994 | Rose |
| 5,277,201 A | 1/1994 | Stern |
| 5,281,220 A | 1/1994 | Blake, III |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,290,287 A | 3/1994 | Boebel et al. |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,312,433 A | 5/1994 | Boebel et al. |
| 5,313,027 A | 5/1994 | Inoue et al. |
| 5,314,445 A | 5/1994 | Degwitz et al. |
| 5,314,463 A | 5/1994 | Camps et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| D349,341 S | 8/1994 | Lichtman et al. |
| 5,334,166 A | 8/1994 | Palestrant |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,359,993 A | 11/1994 | Slater et al. |
| 5,366,477 A | 11/1994 | LeMarie, III et al. |
| 5,367,250 A | 11/1994 | Whisenand |
| 5,368,600 A | 11/1994 | Failla et al. |
| 5,374,277 A | 12/1994 | Hassler |
| 5,376,089 A | 12/1994 | Smith |
| 5,376,094 A | 12/1994 | Kline |
| D354,564 S | 1/1995 | Medema |
| 5,383,875 A | 1/1995 | Bays et al. |
| 5,383,880 A | 1/1995 | Hooven |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,395,360 A | 3/1995 | Manoukian |
| 5,396,194 A | 3/1995 | Williamson et al. |
| 5,396,900 A | 3/1995 | Slater et al. |
| 5,397,325 A | 3/1995 | Della Badia et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| D358,887 S | 5/1995 | Feinberg |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,417,709 A | 5/1995 | Slater |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,277 A | 8/1995 | Dumoulin et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,479 A | 8/1995 | Bressi, Jr. |
| 5,443,480 A | 8/1995 | Jacobs et al. |
| 5,445,622 A | 8/1995 | Brown |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,739 A | 10/1995 | Strand |
| 5,454,809 A | 10/1995 | Janssen |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,476,479 A | 12/1995 | Green et al. |
| 5,478,351 A | 12/1995 | Meade et al. |
| 5,480,406 A | 1/1996 | Nolan et al. |
| 5,480,409 A | 1/1996 | Riza |
| 5,482,054 A | 1/1996 | Slater et al. |

(56) References Cited

U.S. PATENT DOCUMENTS

| | | |
|---|---|---|
| 5,484,436 A | 1/1996 | Eggers et al. |
| 5,493,899 A | 2/1996 | Beck et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,501,654 A | 3/1996 | Failla et al. |
| 5,509,922 A | 4/1996 | Aranyi et al. |
| 5,512,721 A | 4/1996 | Young et al. |
| 5,514,134 A | 5/1996 | Rydell et al. |
| 5,520,702 A | 5/1996 | Sauer et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,549,604 A | 8/1996 | Sutcu et al. |
| 5,554,172 A | 9/1996 | Horner et al. |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,568,859 A | 10/1996 | Levy et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,599,350 A | 2/1997 | Schulze et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,607,436 A | 3/1997 | Pratt et al. |
| 5,611,798 A | 3/1997 | Eggers |
| 5,611,808 A | 3/1997 | Hossain et al. |
| 5,611,813 A | 3/1997 | Lichtman |
| 5,618,294 A | 4/1997 | Aust et al. |
| 5,618,307 A | 4/1997 | Donlon et al. |
| 5,620,415 A | 4/1997 | Lucey et al. |
| 5,620,453 A | 4/1997 | Nallakrishnan |
| 5,620,459 A | 4/1997 | Lichtman |
| 5,624,281 A | 4/1997 | Christensson |
| 5,624,452 A | 4/1997 | Yates |
| 5,626,578 A | 5/1997 | Tihon |
| 5,626,607 A | 5/1997 | Malecki et al. |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,637,111 A | 6/1997 | Sutcu et al. |
| 5,638,003 A | 6/1997 | Hall |
| 5,638,827 A | 6/1997 | Palmer et al. |
| 5,639,403 A | 6/1997 | Ida et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,673,841 A | 10/1997 | Schulze et al. |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,895 A | 2/1998 | Lontine et al. |
| 5,716,366 A | 2/1998 | Yates |
| 5,720,742 A | 2/1998 | Zacharias |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,735,849 A | 4/1998 | Baden et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,762,255 A | 6/1998 | Chrisman et al. |
| 5,762,609 A | 6/1998 | Benaron et al. |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,776,156 A | 7/1998 | Shikhman |
| 5,777,519 A | 7/1998 | Simopoulos |
| 5,779,646 A | 7/1998 | Koblish et al. |
| 5,779,701 A | 7/1998 | McBrayer et al. |
| 5,779,727 A | 7/1998 | Orejola |
| 5,781,048 A | 7/1998 | Nakao et al. |
| H1745 H | 8/1998 | Paraschac |
| 5,791,231 A | 8/1998 | Cohn et al. |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,797,959 A | 8/1998 | Castro et al. |
| 5,800,448 A | 9/1998 | Banko |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,083 A | 10/1998 | Shemesh et al. |
| 5,817,119 A | 10/1998 | Klieman et al. |
| 5,820,630 A | 10/1998 | Lind |
| 5,824,978 A | 10/1998 | Karasik et al. |
| 5,827,271 A * | 10/1998 | Buysse .............. A61B 18/1206 606/34 |

(56) References Cited

U.S. PATENT DOCUMENTS

| | | |
|---|---|---|
| 5,827,274 A | 10/1998 | Bonnet et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,830,212 A | 11/1998 | Cartmell et al. |
| 5,833,690 A | 11/1998 | Yates et al. |
| 5,833,695 A | 11/1998 | Yoon |
| 5,836,072 A | 11/1998 | Sullivan et al. |
| D402,028 S | 12/1998 | Grimm et al. |
| 5,843,080 A | 12/1998 | Fleenor et al. |
| 5,849,020 A | 12/1998 | Long et al. |
| 5,849,022 A | 12/1998 | Sakashita et al. |
| 5,851,214 A | 12/1998 | Larsen et al. |
| 5,853,412 A | 12/1998 | Mayenberger |
| 5,859,527 A | 1/1999 | Cook |
| 5,860,976 A | 1/1999 | Billings et al. |
| 5,865,361 A | 2/1999 | Milliman et al. |
| 5,876,401 A | 3/1999 | Schulze et al. |
| 5,876,410 A | 3/1999 | Petillo |
| 5,876,412 A | 3/1999 | Piraka |
| 5,882,567 A | 3/1999 | Cavallaro et al. |
| D408,018 S | 4/1999 | McNaughton |
| 5,891,141 A | 4/1999 | Rydell |
| 5,891,142 A | 4/1999 | Eggers et al. |
| 5,893,848 A | 4/1999 | Negus et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,907,140 A | 5/1999 | Smith |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,938,589 A | 8/1999 | Wako et al. |
| 5,941,869 A | 8/1999 | Patterson et al. |
| 5,944,562 A | 8/1999 | Christensson |
| 5,944,718 A | 8/1999 | Dafforn et al. |
| 5,951,545 A | 9/1999 | Schilling et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,967,997 A | 10/1999 | Turturro et al. |
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,993,474 A | 11/1999 | Ouchi |
| 5,997,565 A | 12/1999 | Inoue |
| 6,003,517 A | 12/1999 | Sheffield et al. |
| 6,004,332 A | 12/1999 | Yoon et al. |
| 6,004,335 A | 12/1999 | Vaitekunas et al. |
| 6,010,516 A | 1/2000 | Hulka et al. |
| 6,010,519 A | 1/2000 | Mawhirt et al. |
| 6,017,354 A | 1/2000 | Culp et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,995 A | 4/2000 | Durgin |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,056,735 A | 5/2000 | Okada et al. |
| 6,059,782 A | 5/2000 | Novak et al. |
| 6,063,086 A | 5/2000 | Benecke et al. |
| 6,063,103 A | 5/2000 | Hashiguchi |
| 6,066,137 A | 5/2000 | Greep |
| 6,066,139 A | 5/2000 | Ryan et al. |
| 6,071,283 A | 6/2000 | Nardella et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,150 A | 7/2000 | Aznoian et al. |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,090,123 A | 7/2000 | Culp et al. |
| 6,093,186 A * | 7/2000 | Goble ............... A61B 18/1206 606/32 |
| 6,096,037 A | 8/2000 | Mulier et al. |
| 6,099,537 A | 8/2000 | Sugai et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,152,924 A | 11/2000 | Parins |
| 6,159,217 A | 12/2000 | Robie et al. |
| 6,162,220 A | 12/2000 | Nezhat |
| 6,171,316 B1 | 1/2001 | Kovac et al. |
| 6,174,309 B1 | 1/2001 | Wrublewski et al. |
| 6,174,310 B1 | 1/2001 | Kirwan, Jr. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,399 B1 | 2/2001 | Palmer et al. |
| 6,190,400 B1 | 2/2001 | Vandemoer et al. |
| 6,193,709 B1 | 2/2001 | Miyawaki et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |

(56) References Cited

U.S. PATENT DOCUMENTS

| | | |
|---|---|---|
| 6,248,124 B1 | 6/2001 | Pedros et al. |
| 6,248,944 B1 | 6/2001 | Ito |
| 6,249,706 B1 | 6/2001 | Sobota et al. |
| 6,261,307 B1 | 7/2001 | Yoon et al. |
| 6,267,758 B1 | 7/2001 | Daw et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,303,166 B1 | 10/2001 | Kolbe et al. |
| 6,309,404 B1 | 10/2001 | Krzyzanowski |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,329,778 B1 | 12/2001 | Culp et al. |
| 6,334,860 B1 | 1/2002 | Dorn |
| 6,334,861 B1 | 1/2002 | Chandler et al. |
| D453,923 S | 2/2002 | Olson |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,361,534 B1 | 3/2002 | Chen et al. |
| 6,364,876 B1 | 4/2002 | Erb et al. |
| 6,364,879 B1 | 4/2002 | Chen et al. |
| D457,958 S | 5/2002 | Dycus et al. |
| D457,959 S | 5/2002 | Tetzlaff et al. |
| 6,385,265 B1 | 5/2002 | Duffy et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,130 B1 | 8/2002 | Mulier et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,471,696 B1 | 10/2002 | Berube et al. |
| D465,281 S | 11/2002 | Lang |
| D466,209 S | 11/2002 | Bon |
| 6,485,489 B2 | 11/2002 | Teirstein et al. |
| 6,488,680 B1 | 12/2002 | Francischelli et al. |
| 6,494,882 B1 | 12/2002 | Lebouitz et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,536 B2 | 2/2003 | Hooven et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,537,272 B2 | 3/2003 | Christopherson et al. |
| 6,540,745 B1 | 4/2003 | Fairbourn et al. |
| 6,545,239 B2 | 4/2003 | Spedale et al. |
| 6,554,829 B2 | 4/2003 | Schulze et al. |
| 6,554,844 B2 | 4/2003 | Lee et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,610,060 B2 | 8/2003 | Mulier et al. |
| 6,613,048 B2 | 9/2003 | Mulier et al. |
| 6,616,654 B2 | 9/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,623,482 B2 | 9/2003 | Pendekanti et al. |
| 6,626,901 B1 | 9/2003 | Treat et al. |
| 6,629,534 B1 | 10/2003 | St. Goar et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,518 B2 | 11/2003 | Wellman et al. |
| 6,652,521 B2 | 11/2003 | Schulze |
| 6,656,173 B1 | 12/2003 | Palermo |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,666,862 B2 | 12/2003 | Jain et al. |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,704 B2 | 2/2004 | Greep |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,709,445 B2 | 3/2004 | Boebel et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,338 B2 | 6/2004 | Hahnen et al. |
| 6,755,824 B2 | 6/2004 | Jain et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| 6,758,846 B2 | 7/2004 | Goble et al. |
| D493,888 S | 8/2004 | Reschke |
| 6,770,072 B2 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,435 B2 | 8/2004 | Schulze et al. |
| 6,773,441 B1 | 8/2004 | Laufer et al. |
| 6,775,575 B2 | 8/2004 | Bommannan et al. |

(56) References Cited

U.S. PATENT DOCUMENTS

| | | |
|---|---|---|
| 6,776,780 B2 | 8/2004 | Mulier et al. |
| 6,780,181 B2 | 8/2004 | Kroll et al. |
| 6,784,405 B2 | 8/2004 | Flugstad et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,273 B2 | 11/2004 | Mollenauer |
| 6,821,285 B2 | 11/2004 | Laufer et al. |
| 6,824,547 B2 | 11/2004 | Wilson, Jr. et al. |
| 6,830,174 B2 | 12/2004 | Hillstead et al. |
| 6,835,200 B2 | 12/2004 | Laufer et al. |
| 6,843,789 B2 | 1/2005 | Goble |
| 6,857,357 B2 | 2/2005 | Fujii |
| 6,858,028 B2 | 2/2005 | Mulier et al. |
| D502,994 S | 3/2005 | Blake, III |
| 6,860,880 B2 | 3/2005 | Treat et al. |
| 6,878,147 B2 | 4/2005 | Prakash et al. |
| 6,887,240 B1 | 5/2005 | Lands et al. |
| 6,889,116 B2 | 5/2005 | Jinno |
| 6,905,497 B2 | 6/2005 | Truckai et al. |
| 6,908,463 B2 | 6/2005 | Treat et al. |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,951,559 B1 | 10/2005 | Greep |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,974,452 B1 | 12/2005 | Gille et al. |
| 6,976,492 B2 | 12/2005 | Ingle et al. |
| 6,976,992 B2 | 12/2005 | Sachatello et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,989,010 B2 | 1/2006 | Francischelli et al. |
| 6,989,017 B2 | 1/2006 | Howell et al. |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,001,408 B2 | 2/2006 | Knodel et al. |
| 7,011,657 B2 | 3/2006 | Truckai et al. |
| 7,025,763 B2 | 4/2006 | Karasawa et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,699 B2 | 6/2006 | Hess et al. |
| 7,063,715 B2 | 6/2006 | Onuki et al. |
| D525,361 S | 7/2006 | Hushka |
| 7,070,597 B2 | 7/2006 | Truckai et al. |
| 7,083,480 B2 | 8/2006 | Silber |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,108,694 B2 | 9/2006 | Miura et al. |
| 7,112,199 B2 | 9/2006 | Cosmescu |
| 7,112,201 B2 | 9/2006 | Truckai et al. |
| D531,311 S | 10/2006 | Guerra et al. |
| 7,115,123 B2 | 10/2006 | Knowlton et al. |
| 7,115,139 B2 | 10/2006 | McClurken et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse et al. |
| D533,274 S | 12/2006 | Visconti et al. |
| D533,942 S | 12/2006 | Kerr et al. |
| 7,145,757 B2 | 12/2006 | Shea et al. |
| 7,147,632 B2 | 12/2006 | Prakash et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,166,106 B2 | 1/2007 | Bartel et al. |
| 7,169,145 B2 | 1/2007 | Isaacson et al. |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,184,820 B2 | 2/2007 | Jersey-Willuhn et al. |
| D538,932 S | 3/2007 | Malik |
| 7,189,233 B2 | 3/2007 | Truckai et al. |
| 7,195,631 B2 | 3/2007 | Dumbauld |
| D541,418 S | 4/2007 | Schechter et al. |
| 7,204,832 B2 | 4/2007 | Altshuler et al. |
| 7,204,835 B2 | 4/2007 | Latterell et al. |
| 7,207,990 B2 | 4/2007 | Lands et al. |
| 7,208,005 B2 | 4/2007 | Frecker et al. |
| D541,611 S | 5/2007 | Aglassinge |
| D541,938 S | 5/2007 | Kerr et al. |
| 7,211,084 B2 | 5/2007 | Goble et al. |
| 7,223,264 B2 | 5/2007 | Daniel et al. |
| 7,223,265 B2 | 5/2007 | Keppel |
| D545,432 S | 6/2007 | Watanabe |
| 7,232,440 B2 | 6/2007 | Dumbauld et al. |
| D547,154 S | 7/2007 | Lee |
| 7,238,184 B2 | 7/2007 | Megerman et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelto, IV |
| 7,248,944 B2 | 7/2007 | Green |
| 7,252,667 B2 | 8/2007 | Moses et al. |
| 7,254,433 B2 | 8/2007 | Diab et al. |
| 7,255,697 B2 | 8/2007 | Dycus et al. |
| 7,258,688 B1 | 8/2007 | Shah et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,288,103 B2 | 10/2007 | Suzuki |
| 7,291,161 B2 | 11/2007 | Hooven |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |

(56) References Cited

U.S. PATENT DOCUMENTS

| | | |
|---|---|---|
| 7,318,823 B2 | 1/2008 | Sharps et al. |
| 7,326,202 B2 | 2/2008 | McGaffigan |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| 7,347,864 B2 | 3/2008 | Vargas |
| D567,943 S | 4/2008 | Moses et al. |
| 7,354,440 B2 | 4/2008 | Truckal et al. |
| 7,361,172 B2 | 4/2008 | Cimino |
| 7,364,577 B2 | 4/2008 | Wham et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,265 B2 | 7/2008 | Darley et al. |
| 7,396,336 B2 | 7/2008 | Orszulak et al. |
| 7,396,356 B2 | 7/2008 | Mollenauer |
| D575,395 S | 8/2008 | Hushka |
| D575,401 S | 8/2008 | Hixson et al. |
| 7,422,592 B2 | 9/2008 | Morley et al. |
| 7,425,835 B2 | 9/2008 | Eisele |
| 7,431,721 B2 | 10/2008 | Paton et al. |
| 7,435,249 B2 | 10/2008 | Buysse et al. |
| 7,438,714 B2 | 10/2008 | Phan |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,503,474 B2 | 3/2009 | Hillstead et al. |
| 7,510,556 B2 | 3/2009 | Nguyen et al. |
| 7,513,898 B2 | 4/2009 | Johnson et al. |
| 7,517,351 B2 | 4/2009 | Culp et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 7,553,686 B2 | 6/2009 | George et al. |
| 7,569,626 B2 | 8/2009 | Truckai |
| 7,582,087 B2 | 9/2009 | Tetzlaff et al. |
| 7,588,565 B2 | 9/2009 | Marchitto et al. |
| 7,594,313 B2 | 9/2009 | Prakash et al. |
| 7,594,916 B2 | 9/2009 | Weinberg |
| 7,597,693 B2 | 10/2009 | Garrison |
| 7,621,910 B2 | 11/2009 | Sugi |
| 7,624,186 B2 | 11/2009 | Tanida |
| 7,625,370 B2 | 12/2009 | Hart et al. |
| 7,628,791 B2 | 12/2009 | Garrison et al. |
| 7,628,792 B2 | 12/2009 | Guerra |
| 7,637,409 B2 | 12/2009 | Marczyk |
| 7,641,653 B2 | 1/2010 | Dalla Betta et al. |
| 7,651,493 B2 | 1/2010 | Arts et al. |
| 7,651,494 B2 | 1/2010 | McClurken et al. |
| 7,655,004 B2 | 2/2010 | Long |
| 7,655,007 B2 | 2/2010 | Baily |
| 7,668,597 B2 | 2/2010 | Engmark et al. |
| 7,678,111 B2 | 3/2010 | Mulier et al. |
| 7,686,804 B2 | 3/2010 | Johnson et al. |
| 7,686,827 B2 | 3/2010 | Hushka |
| 7,708,735 B2 | 5/2010 | Chapman et al. |
| 7,717,115 B2 | 5/2010 | Barrett et al. |
| 7,717,904 B2 | 5/2010 | Suzuki et al. |
| 7,717,914 B2 | 5/2010 | Kimura |
| 7,717,915 B2 | 5/2010 | Miyazawa |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,727,231 B2 | 6/2010 | Swanson |
| 7,731,717 B2 | 6/2010 | Odom et al. |
| 7,736,374 B2 | 6/2010 | Vaughan et al. |
| 7,744,615 B2 | 6/2010 | Couture |
| 7,749,217 B2 | 7/2010 | Podhajsky |
| 7,753,908 B2 | 7/2010 | Swanson |
| 7,753,909 B2 | 7/2010 | Chapman et al. |
| D621,503 S | 8/2010 | Otten et al. |
| 7,766,910 B2 | 8/2010 | Hixson et al. |
| 7,771,425 B2 | 8/2010 | Dycus et al. |
| 7,776,036 B2 | 8/2010 | Schechter et al. |
| 7,776,037 B2 | 8/2010 | Odom |
| 7,780,662 B2 | 8/2010 | Bahney |
| 7,780,663 B2 | 8/2010 | Yates et al. |
| 7,789,878 B2 | 9/2010 | Dumbauld et al. |
| 7,799,026 B2 | 9/2010 | Schechter et al. |
| 7,799,028 B2 | 9/2010 | Schechter et al. |
| 7,806,892 B2 | 10/2010 | Makin et al. |
| 7,811,283 B2 | 10/2010 | Moses et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| 7,828,798 B2 | 11/2010 | Buysse et al. |
| 7,832,408 B2 | 11/2010 | Shelton, IV et al. |
| 7,837,685 B2 | 11/2010 | Weinberg et al. |
| 7,839,674 B2 | 11/2010 | Lowrey et al. |
| 7,842,033 B2 | 11/2010 | Isaacson et al. |
| 7,846,158 B2 | 12/2010 | Podhajsky |
| 7,846,161 B2 | 12/2010 | Dumbauld et al. |
| 7,857,812 B2 | 12/2010 | Dycus et al. |
| D630,324 S | 1/2011 | Reschke |
| 7,877,852 B2 | 2/2011 | Unger et al. |
| 7,877,853 B2 | 2/2011 | Unger et al. |
| 7,879,035 B2 | 2/2011 | Garrison et al. |
| 7,887,535 B2 | 2/2011 | Lands et al. |
| 7,887,536 B2 | 2/2011 | Johnson et al. |
| 7,896,878 B2 | 3/2011 | Johnson et al. |
| 7,898,288 B2 | 3/2011 | Wong |
| 7,900,805 B2 | 3/2011 | Shelton, IV et al. |
| 7,901,400 B2 | 3/2011 | Wham et al. |
| 7,905,380 B2 | 3/2011 | Shelton, IV et al. |
| 7,905,881 B2 | 3/2011 | Masuda et al. |
| 7,909,820 B2 | 3/2011 | Lipson et al. |
| 7,909,823 B2 | 3/2011 | Moses et al. |
| 7,909,824 B2 | 3/2011 | Masuda et al. |
| 7,918,848 B2 | 4/2011 | Lau et al. |
| 7,922,718 B2 | 4/2011 | Moses et al. |
| 7,922,742 B2 | 4/2011 | Hillstead et al. |
| 7,922,953 B2 | 4/2011 | Guerra |
| 7,931,649 B2 | 4/2011 | Couture et al. |
| 7,935,052 B2 | 5/2011 | Dumbauld |
| 7,945,332 B2 | 5/2011 | Schechter |
| 7,947,041 B2 | 5/2011 | Tetzlaff et al. |
| 7,949,407 B2 | 5/2011 | Kaplan et al. |
| 7,951,149 B2 | 5/2011 | Carlton |
| 7,951,150 B2 | 5/2011 | Johnson et al. |
| 7,955,326 B2 | 6/2011 | Paul et al. |
| 7,955,327 B2 | 6/2011 | Sartor et al. |
| 7,955,331 B2 | 6/2011 | Truckai et al. |
| 7,955,332 B2 | 6/2011 | Arts et al. |
| 7,963,965 B2 | 6/2011 | Buysse et al. |
| 7,967,839 B2 | 6/2011 | Flock et al. |
| 7,972,328 B2 | 7/2011 | Wham et al. |
| 7,972,331 B2 | 7/2011 | Hafner |
| 7,976,544 B2 | 7/2011 | McClurken et al. |
| 7,981,113 B2 | 7/2011 | Truckai et al. |
| 7,988,507 B2 | 8/2011 | Darley et al. |
| 7,998,095 B2 | 8/2011 | McAuley |
| 8,012,150 B2 | 9/2011 | Wham et al. |
| 8,016,827 B2 | 9/2011 | Chojin |
| 8,034,049 B2 | 10/2011 | Odom et al. |
| D649,249 S | 11/2011 | Guerra |
| D649,643 S | 11/2011 | Allen, IV et al. |
| 8,048,074 B2 | 11/2011 | Masuda |
| 8,070,746 B2 | 12/2011 | Orton et al. |

(56) References Cited

U.S. PATENT DOCUMENTS

| | | |
|---|---|---|
| 8,070,748 B2 | 12/2011 | Hixson et al. |
| 8,075,580 B2 | 12/2011 | Makower |
| 8,089,417 B2 | 1/2012 | Popovic et al. |
| 8,092,451 B2 | 1/2012 | Schechter et al. |
| 8,104,956 B2 | 1/2012 | Blaha |
| 8,112,871 B2 | 2/2012 | Brandt et al. |
| 8,114,122 B2 | 2/2012 | Nau, Jr. |
| 8,123,743 B2 | 2/2012 | Arts et al. |
| 8,128,624 B2 | 3/2012 | Couture et al. |
| 8,128,625 B2 | 3/2012 | Odom |
| 8,133,224 B2 | 3/2012 | Geiselhart |
| 8,133,254 B2 | 3/2012 | Dumbauld et al. |
| 8,142,425 B2 | 3/2012 | Eggers |
| 8,142,473 B2 | 3/2012 | Cunningham |
| 8,147,485 B2 | 4/2012 | Wham et al. |
| 8,147,489 B2 | 4/2012 | Moses et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,162,965 B2 | 4/2012 | Reschke et al. |
| 8,162,973 B2 | 4/2012 | Cunningham |
| 8,177,794 B2 | 5/2012 | Cabrera et al. |
| 8,181,649 B2 | 5/2012 | Brunner |
| 8,182,476 B2 | 5/2012 | Julian et al. |
| 8,187,273 B2 | 5/2012 | Kerr et al. |
| D661,394 S | 6/2012 | Romero et al. |
| 8,192,433 B2 | 6/2012 | Johnson et al. |
| 8,192,444 B2 | 6/2012 | Dycus |
| 8,197,479 B2 | 6/2012 | Olson et al. |
| 8,197,633 B2 | 6/2012 | Guerra |
| 8,207,651 B2 | 6/2012 | Gilbert |
| 8,211,105 B2 | 7/2012 | Buysse et al. |
| 8,215,182 B2 | 7/2012 | Artale et al. |
| 8,216,223 B2 | 7/2012 | Wham et al. |
| 8,221,416 B2 | 7/2012 | Townsend |
| 8,226,650 B2 | 7/2012 | Kerr |
| 8,235,992 B2 | 8/2012 | Guerra et al. |
| 8,235,993 B2 | 8/2012 | Hushka et al. |
| 8,236,025 B2 | 8/2012 | Hushka et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,246,618 B2 | 8/2012 | Bucciaglia et al. |
| 8,251,994 B2 | 8/2012 | McKenna et al. |
| 8,251,996 B2 | 8/2012 | Hushka et al. |
| 8,257,352 B2 | 9/2012 | Lawes et al. |
| 8,257,387 B2 | 9/2012 | Cunningham |
| 8,287,528 B2 | 10/2012 | Wham et al. |
| 8,333,765 B2 | 12/2012 | Johnson |
| 8,454,602 B2 | 6/2013 | Kerr |
| 8,523,898 B2 | 9/2013 | Bucciaglia |
| 8,529,566 B2 | 9/2013 | Kappus |
| 8,568,408 B2 | 10/2013 | Townsend |
| 8,591,510 B2 | 11/2013 | Allen, IV |
| 8,628,557 B2 | 1/2014 | Collings |
| 2002/0029036 A1 | 3/2002 | Goble et al. |
| 2002/0107517 A1 | 8/2002 | Witt et al. |
| 2002/0111624 A1 | 8/2002 | Witt et al. |
| 2002/0165469 A1 | 11/2002 | Murakami |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0130653 A1 | 7/2003 | Sixto, Jr. et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0181910 A1 | 9/2003 | Dycus et al. |
| 2003/0191396 A1 | 10/2003 | Sanghvi et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0064151 A1 | 4/2004 | Mollenauer |
| 2004/0115296 A1 | 6/2004 | Duffin |
| 2004/0176779 A1 | 9/2004 | Casutt et al. |
| 2004/0199181 A1 | 10/2004 | Knodel et al. |
| 2004/0224590 A1 | 11/2004 | Rawa et al. |
| 2004/0236326 A1 | 11/2004 | Schulze et al. |
| 2004/0249374 A1 | 12/2004 | Tetzlaff et al. |
| 2004/0260281 A1 | 12/2004 | Baxter, III et al. |
| 2005/0004569 A1 | 1/2005 | Witt et al. |
| 2005/0033278 A1 | 2/2005 | McClurken et al. |
| 2005/0059858 A1 | 3/2005 | Frith et al. |
| 2005/0059934 A1 | 3/2005 | Wenchell et al. |
| 2005/0090817 A1 | 4/2005 | Phan |
| 2005/0096645 A1 | 5/2005 | Wellman et al. |
| 2005/0149017 A1 | 7/2005 | Dycus |
| 2005/0222560 A1 | 10/2005 | Kimura et al. |
| 2005/0254081 A1 | 11/2005 | Ryu et al. |
| 2005/0261588 A1 | 11/2005 | Makin et al. |
| 2005/0283148 A1 | 12/2005 | Janssen et al. |
| 2006/0052779 A1 | 3/2006 | Hammill |
| 2006/0064086 A1 | 3/2006 | Odom |
| 2006/0079933 A1 | 4/2006 | Hushka et al. |
| 2006/0084973 A1 | 4/2006 | Hushka |
| 2006/0111711 A1 | 5/2006 | Goble |
| 2006/0173452 A1 | 8/2006 | Buysse et al. |
| 2006/0190035 A1 | 8/2006 | Hushka et al. |
| 2006/0224053 A1 | 10/2006 | Black et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0271030 A1 | 11/2006 | Francis et al. |
| 2006/0283093 A1 | 12/2006 | Petrovic et al. |
| 2006/0287641 A1 | 12/2006 | Perlin |
| 2007/0027447 A1 | 2/2007 | Theroux et al. |
| 2007/0043353 A1 | 2/2007 | Dycus et al. |
| 2007/0062017 A1 | 3/2007 | Dycus et al. |
| 2007/0118115 A1 | 5/2007 | Artale et al. |
| 2007/0173811 A1 | 7/2007 | Couture et al. |
| 2007/0173813 A1 | 7/2007 | Odom |
| 2007/0198011 A1 | 8/2007 | Sugita |
| 2007/0225695 A1 | 9/2007 | Mayer et al. |
| 2007/0260238 A1 | 11/2007 | Guerra |
| 2007/0260242 A1 | 11/2007 | Dycus et al. |
| 2007/0265616 A1 | 11/2007 | Couture et al. |
| 2007/0265620 A1 | 11/2007 | Kraas et al. |
| 2008/0004616 A1 | 1/2008 | Patrick |
| 2008/0015563 A1 | 1/2008 | Hoey et al. |
| 2008/0015575 A1 | 1/2008 | Odom et al. |
| 2008/0033428 A1 | 2/2008 | Artale et al. |
| 2008/0046122 A1 | 2/2008 | Manzo et al. |
| 2008/0058802 A1 | 3/2008 | Couture et al. |
| 2008/0125797 A1 | 5/2008 | Kelleher |
| 2008/0171938 A1 | 7/2008 | Masuda et al. |
| 2008/0172051 A1 | 7/2008 | Masuda et al. |
| 2008/0215050 A1 | 9/2008 | Bakos |
| 2008/0234672 A1 | 9/2008 | Bastian |
| 2008/0234701 A1 | 9/2008 | Morales et al. |
| 2008/0243106 A1 | 10/2008 | Coe et al. |
| 2008/0243120 A1 | 10/2008 | Lawes et al. |
| 2008/0243158 A1 | 10/2008 | Morgan |
| 2008/0249523 A1 | 10/2008 | McPherson et al. |
| 2008/0249527 A1 | 10/2008 | Couture |
| 2008/0271360 A1 | 11/2008 | Barfield |
| 2008/0281311 A1 | 11/2008 | Dunning et al. |
| 2008/0319292 A1 | 12/2008 | Say et al. |
| 2009/0012520 A1 | 1/2009 | Hixson et al. |
| 2009/0012556 A1 | 1/2009 | Boudreaux et al. |
| 2009/0024126 A1 | 1/2009 | Artale et al. |
| 2009/0036881 A1 | 2/2009 | Artale et al. |
| 2009/0036899 A1 | 2/2009 | Carlton et al. |
| 2009/0043304 A1 | 2/2009 | Tetzlaff et al. |
| 2009/0048596 A1 | 2/2009 | Shields et al. |
| 2009/0054894 A1 | 2/2009 | Yachi |
| 2009/0062794 A1 | 3/2009 | Buysse et al. |
| 2009/0065565 A1 | 3/2009 | Cao |
| 2009/0076506 A1 | 3/2009 | Baker |
| 2009/0082766 A1 | 3/2009 | Unger et al. |
| 2009/0088739 A1 | 4/2009 | Hushka et al. |

(56) References Cited

U.S. PATENT DOCUMENTS

| | | |
|---|---|---|
| 2009/0088745 A1 | 4/2009 | Hushka et al. |
| 2009/0088746 A1 | 4/2009 | Hushka et al. |
| 2009/0088748 A1 | 4/2009 | Guerra et al. |
| 2009/0088750 A1 | 4/2009 | Hushka et al. |
| 2009/0105750 A1 | 4/2009 | Price et al. |
| 2009/0112206 A1 | 4/2009 | Dumbauld et al. |
| 2009/0112229 A1 | 4/2009 | Omori et al. |
| 2009/0131934 A1 | 5/2009 | Odom et al. |
| 2009/0138003 A1 | 5/2009 | Deville et al. |
| 2009/0138006 A1 | 5/2009 | Bales et al. |
| 2009/0149853 A1 | 6/2009 | Shields et al. |
| 2009/0149854 A1 | 6/2009 | Cunningham et al. |
| 2009/0157071 A1 | 6/2009 | Wham et al. |
| 2009/0171354 A1 | 7/2009 | Deville et al. |
| 2009/0177094 A1 | 7/2009 | Brown et al. |
| 2009/0182327 A1 | 7/2009 | Unger |
| 2009/0187188 A1 | 7/2009 | Guerra et al. |
| 2009/0198233 A1 | 8/2009 | Chojin |
| 2009/0204114 A1 | 8/2009 | Odom |
| 2009/0204137 A1 | 8/2009 | Maxwell |
| 2009/0206126 A1 | 8/2009 | Huitema et al. |
| 2009/0209957 A1 | 8/2009 | Schmaltz et al. |
| 2009/0209960 A1 | 8/2009 | Chojin |
| 2009/0234354 A1 | 9/2009 | Johnson et al. |
| 2009/0248007 A1 | 10/2009 | Falkenstein et al. |
| 2009/0248013 A1 | 10/2009 | Falkenstein et al. |
| 2009/0248019 A1 | 10/2009 | Falkenstein et al. |
| 2009/0248020 A1 | 10/2009 | Falkenstein et al. |
| 2009/0248021 A1 | 10/2009 | McKenna |
| 2009/0248022 A1 | 10/2009 | Falkenstein et al. |
| 2009/0248050 A1 | 10/2009 | Hirai |
| 2009/0254080 A1 | 10/2009 | Honda |
| 2009/0254081 A1 | 10/2009 | Allison et al. |
| 2009/0261804 A1 | 10/2009 | McKenna et al. |
| 2009/0270771 A1 | 10/2009 | Takahashi |
| 2009/0275865 A1 | 11/2009 | Zhao et al. |
| 2009/0292282 A9 | 11/2009 | Dycus |
| 2009/0299364 A1 | 12/2009 | Batchelor et al. |
| 2009/0312773 A1 | 12/2009 | Cabrera et al. |
| 2009/0318912 A1 | 12/2009 | Mayer et al. |
| 2010/0016857 A1 | 1/2010 | McKenna et al. |
| 2010/0023009 A1 | 1/2010 | Moses et al. |
| 2010/0036375 A1 | 2/2010 | Regadas |
| 2010/0042143 A1 | 2/2010 | Cunningham |
| 2010/0049187 A1 | 2/2010 | Carlton et al. |
| 2010/0049194 A1 | 2/2010 | Hart et al. |
| 2010/0057078 A1 | 3/2010 | Arts et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0094271 A1 | 4/2010 | Ward et al. |
| 2010/0094287 A1 | 4/2010 | Cunningham et al. |
| 2010/0094289 A1 | 4/2010 | Taylor et al. |
| 2010/0100122 A1 | 4/2010 | Hinton |
| 2010/0130971 A1 | 5/2010 | Baily |
| 2010/0130977 A1 | 5/2010 | Garrison et al. |
| 2010/0168741 A1 | 7/2010 | Sanai et al. |
| 2010/0179543 A1 | 7/2010 | Johnson et al. |
| 2010/0179545 A1 | 7/2010 | Twomey et al. |
| 2010/0179546 A1 | 7/2010 | Cunningham |
| 2010/0179547 A1 | 7/2010 | Cunningham et al. |
| 2010/0198218 A1 | 8/2010 | Manzo |
| 2010/0198248 A1 | 8/2010 | Vakharia |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0217264 A1 | 8/2010 | Odom et al. |
| 2010/0228249 A1 | 9/2010 | Mohr et al. |
| 2010/0228250 A1 | 9/2010 | Brogna |
| 2010/0249769 A1 | 9/2010 | Nau, Jr. et al. |
| 2010/0274160 A1 | 10/2010 | Yachi et al. |
| 2010/0274244 A1 | 10/2010 | Heard |
| 2010/0274265 A1 | 10/2010 | Wingardner et al. |
| 2010/0280511 A1 | 11/2010 | Rachlin et al. |
| 2010/0292691 A1 | 11/2010 | Brogna |
| 2010/0305558 A1 | 12/2010 | Kimura et al. |
| 2010/0307934 A1 | 12/2010 | Chowaniec et al. |
| 2010/0312235 A1 | 12/2010 | Bahney |
| 2010/0331742 A1 | 12/2010 | Masuda |
| 2010/0331839 A1 | 12/2010 | Schechter et al. |
| 2011/0004210 A1 | 1/2011 | Johnson et al. |
| 2011/0015632 A1 | 1/2011 | Artale |
| 2011/0018164 A1 | 1/2011 | Sartor et al. |
| 2011/0034918 A1 | 2/2011 | Reschke |
| 2011/0046623 A1 | 2/2011 | Reschke |
| 2011/0054467 A1 | 3/2011 | Mueller et al. |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0071525 A1 | 3/2011 | Dumbauld et al. |
| 2011/0072638 A1 | 3/2011 | Brandt et al. |
| 2011/0073594 A1 | 3/2011 | Bonn |
| 2011/0077637 A1 | 3/2011 | Brannan |
| 2011/0077648 A1 | 3/2011 | Lee et al. |
| 2011/0077649 A1 | 3/2011 | Kingsley |
| 2011/0082457 A1 | 4/2011 | Kerr et al. |
| 2011/0082494 A1 | 4/2011 | Kerr et al. |
| 2011/0087221 A1 | 4/2011 | Siebrecht et al. |
| 2011/0098689 A1 | 4/2011 | Nau, Jr. et al. |
| 2011/0106079 A1 | 5/2011 | Garrison et al. |
| 2011/0118736 A1 | 5/2011 | Harper et al. |
| 2011/0178519 A1 | 7/2011 | Couture et al. |
| 2011/0184405 A1 | 7/2011 | Mueller |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0238066 A1 | 9/2011 | Olson |
| 2011/0238067 A1 | 9/2011 | Moses et al. |
| 2011/0251605 A1 | 10/2011 | Hoarau et al. |
| 2011/0251606 A1 | 10/2011 | Kerr |
| 2011/0251611 A1 | 10/2011 | Horner et al. |
| 2011/0257680 A1 | 10/2011 | Reschke et al. |
| 2011/0257681 A1 | 10/2011 | Reschke et al. |
| 2011/0270245 A1 | 11/2011 | Horner et al. |
| 2011/0270250 A1 | 11/2011 | Horner et al. |
| 2011/0270251 A1 | 11/2011 | Horner et al. |
| 2011/0270252 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0301592 A1 | 12/2011 | Kerr et al. |
| 2011/0301599 A1 | 12/2011 | Roy et al. |
| 2011/0301600 A1 | 12/2011 | Garrison et al. |
| 2011/0301601 A1 | 12/2011 | Garrison et al. |
| 2011/0301602 A1 | 12/2011 | Roy et al. |
| 2011/0301603 A1 | 12/2011 | Kerr et al. |
| 2011/0301604 A1 | 12/2011 | Horner et al. |
| 2011/0301605 A1 | 12/2011 | Horner |
| 2011/0301606 A1 | 12/2011 | Kerr |
| 2011/0301637 A1 | 12/2011 | Kerr et al. |
| 2011/0319886 A1 | 12/2011 | Chojin et al. |
| 2011/0319888 A1 | 12/2011 | Mueller et al. |
| 2012/0004658 A1 | 1/2012 | Chojin |
| 2012/0010614 A1 | 1/2012 | Couture |
| 2012/0022532 A1 | 1/2012 | Garrison |
| 2012/0029515 A1 | 2/2012 | Couture |

(56) References Cited

U.S. PATENT DOCUMENTS

| | | |
|---|---|---|
| 2012/0041438 A1 | 2/2012 | Nau, Jr. et al. |
| 2012/0046659 A1 | 2/2012 | Mueller |
| 2012/0046660 A1 | 2/2012 | Nau, Jr. |
| 2012/0046662 A1 | 2/2012 | Gilbert |
| 2012/0059371 A1 | 3/2012 | Anderson et al. |
| 2012/0059372 A1 | 3/2012 | Johnson |
| 2012/0059374 A1 | 3/2012 | Johnson et al. |
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0078250 A1 | 3/2012 | Orton et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0095456 A1 | 4/2012 | Schechter et al. |
| 2012/0095460 A1 | 4/2012 | Rooks et al. |
| 2012/0109187 A1 | 5/2012 | Gerhardt, Jr. et al. |
| 2012/0118507 A1 | 5/2012 | Brandt et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0123413 A1 | 5/2012 | Chernov et al. |
| 2012/0130367 A1 | 5/2012 | Garrison |
| 2012/0136353 A1 | 5/2012 | Romero |
| 2012/0136354 A1 | 5/2012 | Rupp |
| 2012/0143185 A1 | 6/2012 | Nau, Jr. |
| 2012/0165797 A1 | 6/2012 | Cunningham |
| 2012/0165818 A1 | 6/2012 | Odom |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0172925 A1 | 7/2012 | Dumbauld et al. |
| 2012/0184989 A1 | 7/2012 | Twomey |
| 2012/0184990 A1 | 7/2012 | Twomey |
| 2012/0202179 A1 | 8/2012 | Fedotov et al. |
| 2012/0209263 A1 | 8/2012 | Sharp et al. |
| 2012/0215219 A1 | 8/2012 | Roy et al. |
| 2012/0215242 A1 | 8/2012 | Reschke et al. |
| 2012/0226276 A1 | 9/2012 | Dycus |
| 2012/0239034 A1 | 9/2012 | Horner |
| 2012/0253344 A1 | 10/2012 | Dumbauld |
| 2012/0259331 A1 | 10/2012 | Garrison |
| 2012/0265241 A1 | 10/2012 | Hart |
| 2012/0283727 A1 | 11/2012 | Twomey |
| 2012/0283734 A1 | 11/2012 | Ourada |
| 2012/0296205 A1 | 11/2012 | Chernov |
| 2012/0296238 A1 | 11/2012 | Chernov |
| 2012/0296239 A1 | 11/2012 | Chernov |
| 2012/0296317 A1 | 11/2012 | Chernov |
| 2012/0296323 A1 | 11/2012 | Chernov |
| 2012/0296324 A1 | 11/2012 | Chernov |
| 2012/0296332 A1 | 11/2012 | Chernov |
| 2012/0296333 A1 | 11/2012 | Twomey |
| 2012/0296334 A1 | 11/2012 | Kharin |
| 2012/0296371 A1 | 11/2012 | Kappus |
| 2012/0303021 A1 | 11/2012 | Guerra |
| 2012/0303025 A1 | 11/2012 | Garrison |
| 2012/0303026 A1 | 11/2012 | Dycus |
| 2012/0310240 A1 | 12/2012 | Olson |
| 2012/0316601 A1 | 12/2012 | Twomey |
| 2012/0323238 A1 | 12/2012 | Tyrell |
| 2012/0330308 A1 | 12/2012 | Joseph |
| 2012/0330309 A1 | 12/2012 | Joseph |
| 2013/0014375 A1 | 1/2013 | Hempstead |
| 2013/0018364 A1 | 1/2013 | Chernov |
| 2013/0018371 A1 | 1/2013 | Twomey |
| 2013/0018372 A1 | 1/2013 | Sims |
| 2013/0022495 A1 | 1/2013 | Allen, IV |
| 2013/0041370 A1 | 2/2013 | Unger |
| 2013/0041402 A1 | 2/2013 | Chojin |
| 2013/0046295 A1 | 2/2013 | Kerr |
| 2013/0046303 A1 | 2/2013 | Evans |
| 2013/0046306 A1 | 2/2013 | Evans |
| 2013/0046337 A1 | 2/2013 | Evans |
| 2013/0060250 A1 | 3/2013 | Twomey |
| 2013/0066303 A1 | 3/2013 | Hart |
| 2013/0066318 A1 | 3/2013 | Kerr |
| 2013/0071282 A1 | 3/2013 | Fry |
| 2013/0072919 A1 | 3/2013 | Allen, IV |
| 2013/0072927 A1 | 3/2013 | Allen, IV |
| 2013/0079760 A1 | 3/2013 | Twomey |
| 2013/0079762 A1 | 3/2013 | Twomey |
| 2013/0079774 A1 | 3/2013 | Whitney |
| 2013/0082035 A1 | 4/2013 | Allen, IV |
| 2013/0085491 A1 | 4/2013 | Twomey |
| 2013/0085496 A1 | 4/2013 | Unger |
| 2013/0085516 A1 | 4/2013 | Kerr |
| 2013/0103030 A1 | 4/2013 | Garrison |
| 2013/0103031 A1 | 4/2013 | Garrison |
| 2013/0103035 A1 | 4/2013 | Horner |
| 2013/0123837 A1 | 5/2013 | Roy |
| 2013/0138101 A1 | 5/2013 | Kerr |
| 2013/0138102 A1 | 5/2013 | Twomey |
| 2013/0138129 A1 | 5/2013 | Garrison |
| 2013/0144284 A1 | 6/2013 | Behnke, II |
| 2013/0150842 A1 | 6/2013 | Nau, Jr. |
| 2013/0178852 A1 | 7/2013 | Allen, IV |
| 2013/0185922 A1 | 7/2013 | Twomey |
| 2013/0190753 A1 | 7/2013 | Garrison |
| 2013/0190760 A1 | 7/2013 | Allen, IV |
| 2013/0197503 A1 | 8/2013 | Orszulak |
| 2013/0218198 A1 | 8/2013 | Larson |
| 2013/0226177 A1 | 8/2013 | Brandt |
| 2013/0226178 A1 | 8/2013 | Brandt |
| 2013/0232753 A1 | 9/2013 | Ackley |
| 2013/0238016 A1 | 9/2013 | Garrison |
| 2013/0245623 A1 | 9/2013 | Twomey |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0270322 A1 | 10/2013 | Scheib et al. |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296848 A1 | 11/2013 | Allen, IV et al. |
| 2013/0296854 A1 | 11/2013 | Mueller |
| 2013/0296856 A1 | 11/2013 | Unger et al. |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325043 A1 | 12/2013 | Butcher |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0031821 A1 | 1/2014 | Garrison |
| 2014/0031860 A1 | 1/2014 | Stoddard |
| 2014/0046323 A1 | 2/2014 | Payne |
| 2014/0058385 A1 | 2/2014 | Wham |
| 2014/0066910 A1 | 3/2014 | Nau |
| 2014/0066911 A1 | 3/2014 | Nau |
| 2014/0074091 A1 | 3/2014 | Arya |

FOREIGN PATENT DOCUMENTS

| | | |
|---|---|---|
| CA | 2 590 520 | 11/2007 |
| CN | 201299462 | 9/2009 |
| DE | 2415263 | 10/1975 |
| DE | 2514501 | 10/1976 |
| DE | 2627679 | 1/1977 |
| DE | 3423356 | 1/1986 |
| DE | 3612646 | 4/1987 |
| DE | 3627221 | 2/1988 |
| DE | 8712328 | 3/1988 |
| DE | 0364216 | 4/1990 |

(56) References Cited

FOREIGN PATENT DOCUMENTS

| | | |
|---|---|---|
| DE | 4303882 | 8/1994 |
| DE | 19506363 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 10045375 | 4/2002 |
| DE | 20121161 | 4/2002 |
| DE | 10 2004 026 179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 623316 | 5/1949 |
| EP | 0467501 | 1/1992 |
| EP | 0509670 | 10/1992 |
| EP | 0518230 | 12/1992 |
| EP | 0541930 | 5/1993 |
| EP | 0306123 | 8/1993 |
| EP | 0572131 | 12/1993 |
| EP | 0584787 | 3/1994 |
| EP | 0589453 | 3/1994 |
| EP | 0589555 | 3/1994 |
| EP | 0623316 | 11/1994 |
| EP | 0624348 | 11/1994 |
| EP | 0640317 | 3/1995 |
| EP | 0648475 | 4/1995 |
| EP | 0650701 | 5/1995 |
| EP | 0694290 | 3/1996 |
| EP | 0717966 | 6/1996 |
| EP | 0754437 | 3/1997 |
| EP | 0517243 | 9/1997 |
| EP | 0853922 | 7/1998 |
| EP | 0875209 | 11/1998 |
| EP | 0878169 | 11/1998 |
| EP | 0887046 | 1/1999 |
| EP | 0888747 | 1/1999 |
| EP | 0923907 | 1/1999 |
| EP | 0913126 | 5/1999 |
| EP | 0950378 | 10/1999 |
| EP | 0986990 | 3/2000 |
| EP | 1034747 | 9/2000 |
| EP | 1034748 | 9/2000 |
| EP | 1025807 | 10/2000 |
| EP | 1034746 | 10/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1159926 | 12/2001 |
| EP | 1177771 | 2/2002 |
| EP | 1278007 | 1/2003 |
| EP | 1301135 | 4/2003 |
| EP | 1330991 | 7/2003 |
| EP | 1486177 | 6/2004 |
| EP | 1472984 | 11/2004 |
| EP | 0774232 | 1/2005 |
| EP | 1527747 | 5/2005 |
| EP | 1530952 | 5/2005 |
| EP | 1532932 | 5/2005 |
| EP | 1535581 | 6/2005 |
| EP | 1281878 | 10/2005 |
| EP | 1609430 | 12/2005 |
| EP | 1201192 | 2/2006 |
| EP | 1632192 | 3/2006 |
| EP | 1186274 | 4/2006 |
| EP | 1642543 | 4/2006 |
| EP | 1645238 | 4/2006 |
| EP | 1645240 | 4/2006 |
| EP | 1649821 | 4/2006 |
| EP | 1685806 | 8/2006 |
| EP | 1707143 | 10/2006 |
| EP | 1545360 | 3/2007 |
| EP | 1767163 | 3/2007 |
| EP | 1767164 | 3/2007 |
| EP | 1769765 | 4/2007 |
| EP | 1769766 | 4/2007 |
| EP | 1772109 | 4/2007 |
| EP | 1785097 | 5/2007 |
| EP | 1785098 | 5/2007 |
| EP | 1785101 | 5/2007 |
| EP | 1787597 | 5/2007 |
| EP | 1810625 | 7/2007 |
| EP | 1810628 | 7/2007 |
| EP | 1842500 | 10/2007 |
| EP | 1878400 | 1/2008 |
| EP | 1894535 | 3/2008 |
| EP | 1929970 | 6/2008 |
| EP | 1946715 | 7/2008 |
| EP | 1958583 | 8/2008 |
| EP | 1990019 | 11/2008 |
| EP | 1994904 | 11/2008 |
| EP | 1683496 | 12/2008 |
| EP | 1997438 | 12/2008 |
| EP | 1997439 | 12/2008 |
| EP | 1527744 | 2/2009 |
| EP | 2103268 | 8/2009 |
| EP | 2105104 | 9/2009 |
| EP | 2147649 | 1/2010 |
| EP | 2153791 | 2/2010 |
| EP | 2206474 | 7/2010 |
| EP | 1920725 | 10/2010 |
| EP | 2243439 | 10/2010 |
| EP | 2294998 | 3/2011 |
| EP | 2301467 | 3/2011 |
| EP | 1628586 | 7/2011 |
| GB | 1490585 | 11/1977 |
| GB | 2214430 | 6/1989 |
| GB | 2213416 | 8/1989 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47149 | 2/1999 |
| JP | 11-47150 | 2/1999 |
| JP | 11-169381 | 6/1999 |
| JP | 11-192238 | 7/1999 |
| JP | 11-244298 | 9/1999 |
| JP | 2000-135222 | 5/2000 |
| JP | 2000-342599 | 12/2000 |
| JP | 2000-350732 | 12/2000 |
| JP | 2001-8944 | 1/2001 |
| JP | 2001-29355 | 2/2001 |
| JP | 2001-29356 | 2/2001 |
| JP | 2001-128990 | 5/2001 |
| JP | 2001-190564 | 7/2001 |

(56) References Cited

FOREIGN PATENT DOCUMENTS

| | | |
|---|---|---|
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2005-312807 | 10/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/19681 | 10/1993 |
| WO | WO 93/21845 | 11/1993 |
| WO | WO 94/00059 | 1/1994 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 95/20360 | 8/1995 |
| WO | WO 95/20921 | 8/1995 |
| WO | WO 96/05776 | 2/1996 |
| WO | WO 96/11635 | 4/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/18768 | 5/1997 |
| WO | WO 97/24073 | 7/1997 |
| WO | WO 97/24993 | 7/1997 |
| WO | WO 98/14124 | 4/1998 |
| WO | WO 98/27880 | 7/1998 |
| WO | WO 98/31290 | 7/1998 |
| WO | WO 98/43264 | 10/1998 |
| WO | WO 99/03407 | 1/1999 |
| WO | WO 99/03408 | 1/1999 |
| WO | WO 99/03409 | 1/1999 |
| WO | WO 99/03414 | 1/1999 |
| WO | WO 99/12488 | 3/1999 |
| WO | WO 99/23933 | 5/1999 |
| WO | WO 99/23959 | 5/1999 |
| WO | WO 99/25261 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24322 | 5/2000 |
| WO | WO 00/24330 | 5/2000 |
| WO | WO 00/24331 | 5/2000 |
| WO | WO 00/33753 | 6/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 00/59392 | 10/2000 |
| WO | WO 01/00114 | 1/2001 |
| WO | WO 01/01847 | 1/2001 |
| WO | WO 01/15614 | 3/2001 |
| WO | WO 01/17448 | 3/2001 |
| WO | WO 01/54604 | 8/2001 |
| WO | WO 01/66025 | 9/2001 |
| WO | WO 02/07627 | 1/2002 |
| WO | WO 02/45589 | 6/2002 |
| WO | WO 02/058544 | 8/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 02/085218 | 10/2002 |
| WO | WO 02/094746 | 11/2002 |
| WO | WO 03/061500 | 7/2003 |
| WO | WO 03/068046 | 8/2003 |
| WO | WO 03/090630 | 11/2003 |
| WO | WO 03/096880 | 11/2003 |
| WO | WO 03/101311 | 12/2003 |
| WO | WO 2004/028585 | 4/2004 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/083797 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/009255 | 2/2005 |
| WO | WO 2005/011049 | 2/2005 |
| WO | WO 2005/030071 | 4/2005 |
| WO | WO 2005/048809 | 6/2005 |
| WO | WO 2005/050151 | 6/2005 |
| WO | WO 2005/110264 | 11/2005 |
| WO | WO 2006/021269 | 3/2006 |
| WO | WO 2008/008457 | 1/2008 |
| WO | WO 2008/040483 | 4/2008 |
| WO | WO 2008/045348 | 4/2008 |
| WO | WO 2008/045350 | 4/2008 |
| WO | WO 2008/112147 | 9/2008 |
| WO | WO 2009/005850 | 1/2009 |
| WO | WO 2009/032623 | 3/2009 |
| WO | WO 2009/039179 | 3/2009 |
| WO | WO 2009/039510 | 3/2009 |
| WO | WO 2009/124097 | 10/2009 |
| WO | WO 2010/104753 | 9/2010 |
| WO | WO 2011/018154 | 2/2011 |

OTHER PUBLICATIONS

U.S. Appl. No. 09/177,950, filed Oct. 23, 1998, Frazier.
U.S. Appl. No. 09/387,883, filed Sep. 1, 1999, Schmaltz.
U.S. Appl. No. 09/591,328, filed Jun. 9, 2000, Ryan.
U.S. Appl. No. 12/336,970, filed Dec. 17, 2008, Sremeich.
U.S. Appl. No. 13/708,335, filed Dec. 7, 2012, Dumbauld.
U.S. Appl. No. 13/731,674, filed Dec. 31, 2012, Siebrecht.
U.S. Appl. No. 14/019,031, filed Sep. 5, 2013, Garrison.
U.S. Appl. No. 14/019,094, filed Sep. 5, 2013, Garrison.
U.S. Appl. No. 14/032,486, filed Sep. 20, 2013, Kendrick.
U.S. Appl. No. 14/035,423, filed Sep. 24, 2013, Garrison.
U.S. Appl. No. 14/037,772, filed Sep. 26, 2013, Frushour.
U.S. Appl. No. 14/041,995, filed Sep. 30, 2013, Kendrick.
U.S. Appl. No. 14/042,947, filed Oct. 1, 2013, Craig.
U.S. Appl. No. 14/043,039, filed Oct. 1, 2013, Rusin.
U.S. Appl. No. 14/043,322, filed Oct. 1, 2013, O'Neill.
U.S. Appl. No. 14/047,474, filed Oct. 7, 2013, Mueller.
U.S. Appl. No. 14/050,593, filed Oct. 10, 2013, Plaven.
U.S. Appl. No. 14/052,827, filed Oct. 14, 2013, Nau.
U.S. Appl. No. 14/052,856, filed Oct. 14, 2013, Latimer.
U.S. Appl. No. 14/052,871, filed Oct. 14, 2013, Kappus.
U.S. Appl. No. 14/054,173, filed Oct. 15, 2013, Payne.
U.S. Appl. No. 14/054,573, filed Oct. 15, 2013, Harper.
U.S. Appl. No. 14/064,310, filed Oct. 28, 2013, Reschke.
U.S. Appl. No. 14/064,702, filed Oct. 28, 2013, Townsend.
U.S. Appl. No. 14/065,644, filed Oct. 29, 2013, Reschke.
U.S. Appl. No. 14/072,386, filed Nov. 5, 2014, Wham.

(56) References Cited

OTHER PUBLICATIONS

U.S. Appl. No. 14/080,564, filed Nov. 14, 2013, Lawes.
U.S. Appl. No. 14/080,581, filed Nov. 14, 2013, Kerr.
U.S. Appl. No. 14/083,696, filed Nov. 19, 2013, Homer.
U.S. Appl. No. 14/086,399, filed Nov. 21, 2013, Allen.
U.S. Appl. No. 14/091,505, filed Nov. 27, 2013, Garrison.
U.S. Appl. No. 14/091,521, filed Nov. 27, 2013, Garrison.
U.S. Appl. No. 14/091,532, filed Nov. 27, 2013, Garrison.
U.S. Appl. No. 14/098,953, filed Dec. 6, 2013, Cunningham.
U.S. Appl. No. 14/100,237, filed Dec. 9, 2013, Reschke.
U.S. Appl. No. 14/103,971, filed Dec. 12, 2013, Roy.
U.S. Appl. No. 14/105,374, filed Dec. 13, 2013, Moua.
U.S. Appl. No. 14/109,459, filed Dec. 17, 2013, Hoarau.
U.S. Appl. No. 14/149,343, filed Jan. 7, 2014, Schmaltz.
U.S. Appl. No. 14/152,618, filed Jan. 10, 2014, Artale.
U.S. Appl. No. 14/152,690, filed Jan. 10, 2014, Hart.
U.S. Appl. No. 14/153,346, filed Jan. 13, 2014, Collings.
U.S. Appl. No. 14/162,192, filed Jan. 23, 2014, Garrison.
U.S. Appl. No. 08/177,950, filed Oct. 23, 1998, Frazier.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview". Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

\* cited by examiner

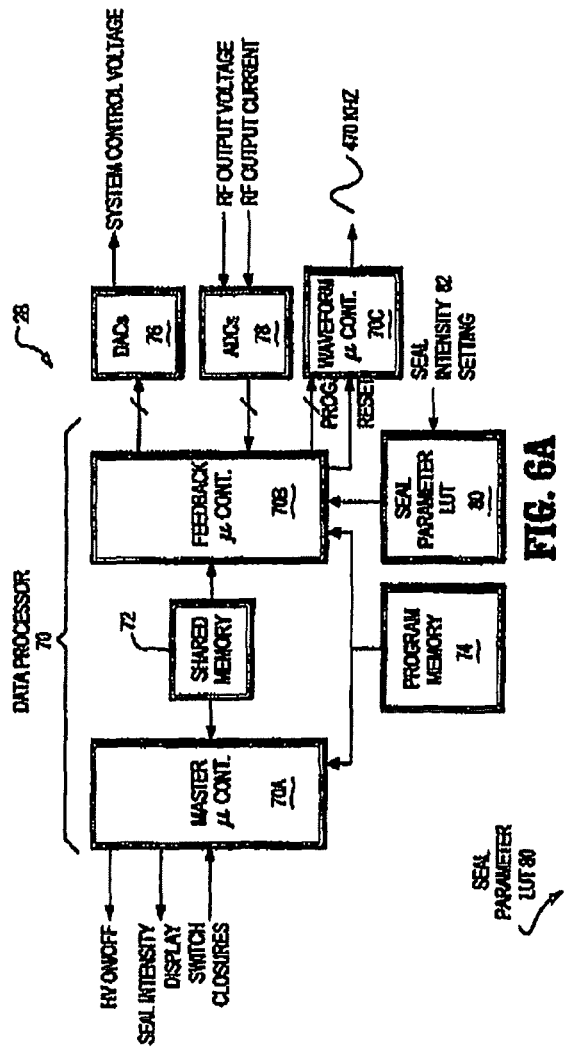

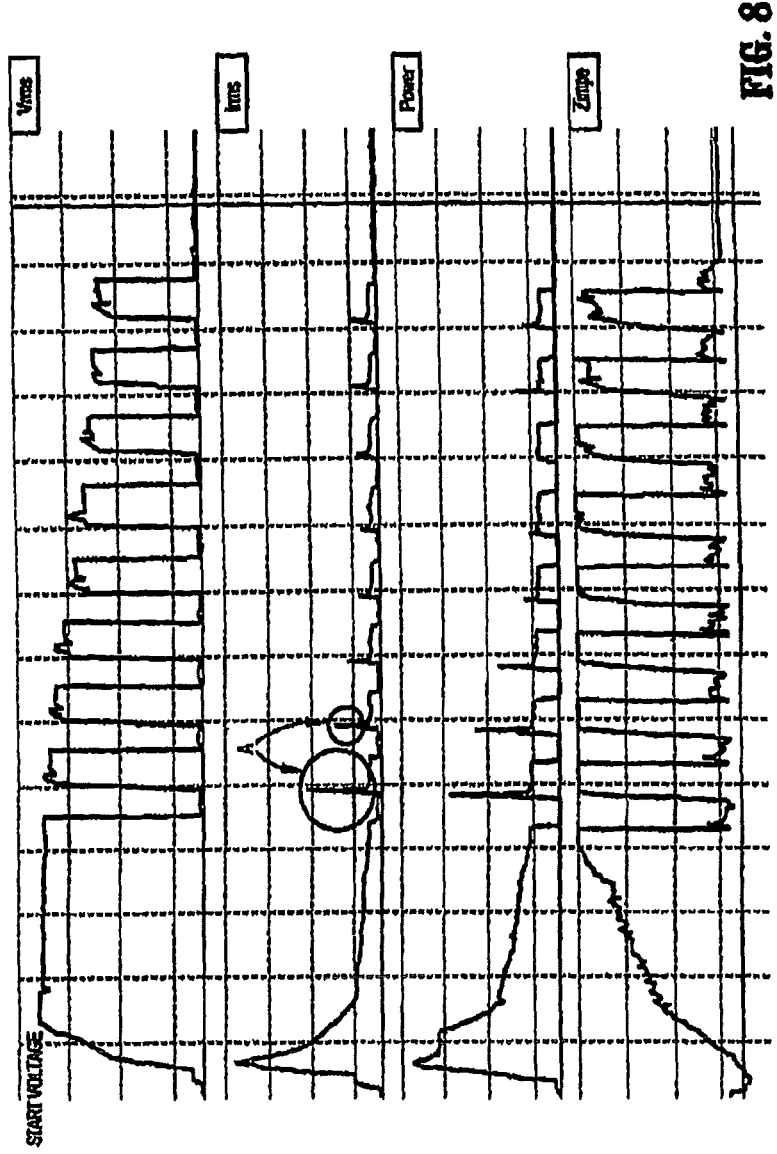

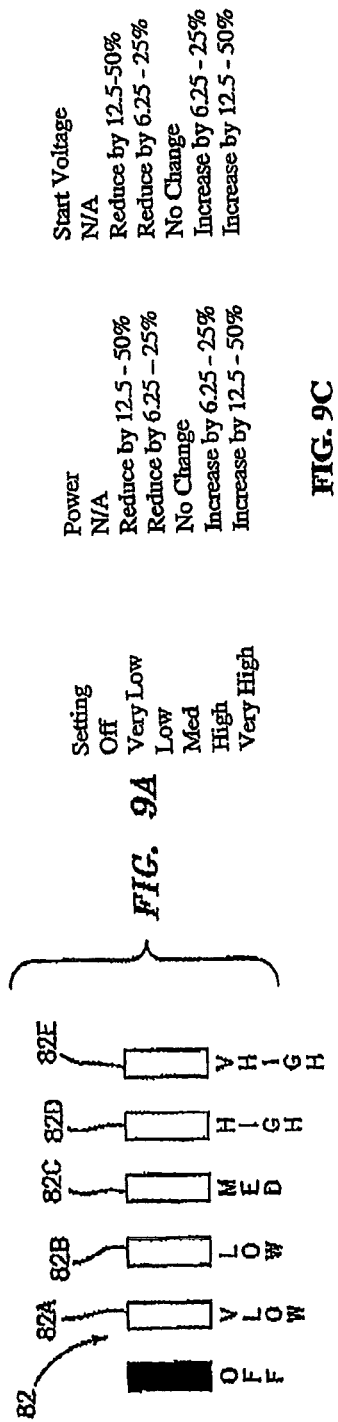

FIG. 9A

| Setting | Power | Start Voltage |
|---|---|---|
| Off | N/A | N/A |
| Very Low | Reduce by 12.5-50% | Reduce by 12.5-50% |
| Low | Reduce by 6.25-25% | Reduce by 6.25-25% |
| Med | No Change | No Change |
| High | Increase by 6.25-25% | Increase by 6.25-25% |
| Very High | Increase by 12.5-50% | Increase by 12.5-50% |

FIG. 9C

| Setting | Power | Start Voltage |
|---|---|---|
| Off | N/A | N/A |
| Very Low | Reduce by 25% | Reduce by 25% |
| Low | Reduce by 12% | Reduce by 12% |
| Med | No Change | No Change |
| High | No Change | Increase by 12% |
| Very High | No Change | Increase by 25% |

| Voltage Decay | Dwell Time |
|---|---|
| N/A | N/A |
| Increase by 12% | Reduce by 12.5% |
| Increase by 6% | Reduce by 6.25% |
| No Change | No Change |
| Reduce by 6% | Increase by 6.25% |
| Reduce by 12% | Increase by 12.5% |

FIG. 9B

VESSEL SEALING SYSTEM

CROSS REFERENCE TO RELATED APPLICATIONS

The present application is a continuation of U.S. patent application Ser. No. 13/652,932, entitled "Vessel Sealing System", by Robert Wham et al., now U.S. Pat. No. 8,591,506, which is a continuation of U.S. patent application Ser. No. 12/057,557 entitled "Vessel Sealing System", by Robert Wham et al., now U.S. Pat. No. 8,287,528, which is a continuation of U.S. patent application Ser. No. 10/626,390 also entitled "Vessel Sealing System", by Robert Wham et al., now U.S. Pat. No. 7,364,577, which is a continuation-in-part application of U.S. patent application Ser. No. 10/073,761 also entitled "Vessel Sealing System", by Robert Wham et al., now U.S. Pat. No. 6,796,981, which is a continuation-in-part of U.S. patent application Ser. No. 09/408,944 also entitled "Vessel Sealing System", by Robert Wham et al., now U.S. Pat. No. 6,398,779, and which claims priority to U.S. Provisional Patent Application Ser. No. 60/105,417 filed on Oct. 23, 1998. The disclosure of each Patent Application is incorporated by reference herein in its entirety.

FIELD

This invention relates generally to medical instruments and, in particular, to generators that provide radio frequency (RF) energy useful in sealing tissue and vessels during electrosurgical and other procedures. Electrosurgical generators are employed by surgeons to cut and coagulate the tissue of a patient.

BACKGROUND

High frequency electrical power, which may be also referred to as radio frequency (RF) power or energy, is produced by the electrosurgical generator and applied to the tissue by an electrosurgical tool. Both monopolar and bipolar configurations are commonly used during electrosurgical procedures.

Electrosurgical techniques can be used to seal small diameter blood vessels and vascular bundles. Another application of electrosurgical techniques is in tissue fusion wherein two layers of tissue are grasped and clamped together by a suitable electrosurgical tool while the electrosurgical RF energy is applied. The two layers of tissue are then fused together.

At this point it is significant to note that the process of coagulating small vessels is fundamentally different than vessel sealing or tissue fusion. For the purposes herein the term coagulation can be defined as a process of desiccating tissue wherein the tissue cells are ruptured and dried. Vessel sealing or tissue fusion can both be defined as desiccating tissue by the process of liquefying the collagen in the tissue so that it crosslinks and reforms into a fused mass. Thus, the coagulation of small vessels if generally sufficient to close them, however, larger vessels normally need to be sealed to assure permanent closure.

However, and as employed herein, the term "electrosurgical desiccation" is intended to encompass any tissue desiccation procedure, including electrosurgical coagulation, desiccation, vessel sealing, and tissue fusion.

One of the problems that can arise from electrosurgical desiccation is undesirable tissue damage due to thermal effects, wherein otherwise healthy tissue surrounding the tissue to which the electrosurgical energy is being applied is thermally damaged by an effect known in the art as "thermal spread". During the occurrence of thermal spread excess heat from the operative site can be directly conducted to the adjacent tissue, and/or the release of steam from the tissue being treated at the operative site can result in damage to the surrounding tissue.

It can be appreciated that it would be desirable to provide an electrosurgical generator that limited the possibility of the occurrence of thermal spread.

Another problem that can arise with conventional electrosurgical techniques is a buildup of eschar on the electrosurgical tool or instrument. Eschar is a deposit that forms on working surface(s) of the tool, and results from tissue that is electrosurgically desiccated and then charred. One result of the buildup of eschar is a reduction in the effectiveness of the surgical tool. The buildup of eschar on the electrosurgical tool can be reduced if less heat is developed at the operative site.

It has been well established that a measurement of the electrical impedance of tissue provides an indication of the state of desiccation of the tissue, and this observation has been utilized in some electrosurgical generators to automatically terminate the generation of electrosurgical power based on a measurement of tissue impedance.

At least two techniques for determining an optimal amount of desiccation are known by those skilled in this art. One technique sets a threshold impedance, and terminates electrosurgical power when the measured tissue impedance crosses the threshold. A second technique terminates the generation of electrosurgical power based on dynamic variations in the tissue impedance.

A discussion of the dynamic variations of tissue impedance can be found in a publication entitled "Automatically Controlled Bipolar Electrocoagulation", Neurosurgical Review, 7:2-3, pp. 187-190, 1984, by Vallfors and Bergdahl. FIG. 2 of this publication depicts the impedance as a function of time during the heating of a tissue, and the authors reported that the impedance value of tissue was observed to be near to a minimum value at the moment of coagulation. Based on this observation, the authors suggest a micro-computer technique for monitoring the minimum impedance and subsequently terminating the output power to avoid charring the tissue.

Another publication by the same authors, "Studies on Coagulation and the Development of an Automatic Computerized Bipolar Coagulator", Journal of Neurosurgery, 75:1, pp. 148-151, July 1991, discusses the impedance behavior of tissue and its application to electrosurgical vessel sealing, and reports that the impedance has a minimum value at the moment of coagulation.

The following U.S. Patents are also of interest in this area. U.S. Pat. No. 5,540,684, Hassler, Jr. addresses the problem associated with turning off the RF energy output automatically after the tissue impedance has fallen from a predetermined maximum, subsequently risen from a predetermined minimum and then reached a particular threshold. A storage device records maximum and minimum impedance values, and a circuit determines the threshold. U.S. Pat. No. 5,472,443, Cordis et al., discusses a variation of tissue impedance with temperature, wherein the impedance is shown to fall, and then to rise, as the temperature is increased. FIG. 2 of this patent shows a relatively lower temperature Region A where salts contained in body fluids are believed to dissociate, thereby decreasing the electrical impedance. A relatively next higher temperature Region B is where the water in the tissue boils away, causing the impedance to rise. The next relatively higher temperature Region C is where the tissue becomes charred, which results in a slight lowering of the electrical impedance. U.S. Pat. No. 4,191,188, Belt et al., discloses the use of two timers whose duty cycles are simultaneously and proportionately adjusted so that high frequency signal bursts are constantly centered about the peak power point, regardless of duty cycle variations.

Also of interest is U.S. Pat. No. 5,827,271, Buysse et al., "Energy Delivery System for Vessel Sealing", which employs a surgical tool capable of grasping a tissue and applying an appropriate amount of closure force to the tissue, and for then conducting electrosurgical energy to the tissue concurrently with the application of the closure force. FIG. 2 of this patent, shown herein as FIG. 1 for depicting the prior art, illustrates a set of power curves which represent the electrosurgical power delivered to the tissue as a function of the tissue impedance. At low impedances, the electrosurgical power is increased by rapidly increasing the output current. The increase in electrosurgical power is terminated when a first impedance breakpoint, labeled as 1, is reached (e.g. <20 ohms). Next, the electrosurgical power is held approximately constant until proteins in the vessels and other tissues have melted. The impedance at which this segment ends varies in accordance with the magnitude of the RMS power. For example, where the maximum RMS power is approximately 125 Watts, the segment (B) ends at about 128 ohms. When a lower power is used (e.g., 75 Watts), the segment (C) may end at an impedance value of 256 ohms. Next, the output power is lowered to less than one half the maximum value, and the lower power delivery is terminated when a second impedance breakpoint is reached (2.048×103 ohms). Alternatives to using the impedance for determining the second breakpoint are the use of I-V phase angle, or the magnitude of the output current.

Based on the foregoing it should be evident that electrosurgery requires the controlled application of RF energy to an operative tissue site. To achieve successful clinical results during surgery, the electrosurgical generator should produce a controlled output RF signal having an amplitude and wave shape that is applied to the tissue within predetermined operating levels. However, problems can arise during electrosurgery when rapid desiccation of tissue occurs resulting in excess RF levels being applied to the tissue. These excess levels produce less than desirable tissue effects, which can increase thermal spread, or can cause tissue charring and may shred and disintegrate tissue. It would be desirable to provide a system with more controlled output to improve vessel sealing and reduce damage to surrounding tissue. The factors that affect vessel sealing include the surgical instrument utilized, as well as the generator for applying RF energy to the instrument jaws. It has been recognized that the gap between the instrument jaws and the pressure of the jaws against the tissue affect tissue sealing because of their impact on current flow. For example, insufficient pressure or an excessive gap will not supply sufficient energy to the tissue and could result in an inadequate seal.

However, it has also been recognized that the application of RF energy also affects the seal. For example, pulsing of RF energy will improve the seal. This is because the tissue loses moisture as it desiccates and by stopping or significantly lowering the output the generator between pulses, this allows some moisture to return to the tissue for the application of next RF pulse. It has also been recognized by the inventors that varying each pulse dependent on certain parameters is also advantageous in providing an improved seal. Thus, it would be advantageous to provide a vessel sealing system which better controls RF energy and which can be varied at the outset of the procedure to accommodate different tissue structures, and which can further be varied during the procedure itself to accommodate changes in the tissue as it desiccates.

An accommodation for overvoltage clamping is also desirable. In this regard, conventional overvoltage techniques use a means of clamping or clipping the excess overvoltage using avalanche devices such as diodes, zener diodes and transorbs so as to limit the operating levels. In these techniques the excess energy, as well as the forward conduction energy, is absorbed by the protection device and inefficiently dissipated in the form of heat. More advanced prior art techniques actively clamp only the excess energy using a predetermined comparator reference value, but still absorb and dissipate the excess energy in the form of heat.

U.S. Pat. No. 5,594,636 discloses a system for AC to AC power conversion using switched commutation. This system addresses overvoltage conditions which occur during switched commutation by incorporating an active output voltage sensing and clamping using an active clamp voltage regulator which energizes to limit the output. The active clamp switches in a resistive load to dissipate the excess energy caused by the overvoltage condition.

Other patents in this area include U.S. Pat. No. 5,500,616, which discloses an overvoltage clamp circuit, and U.S. Pat. No. 5,596,466, which discloses an isolated half-bridge power module. Both of these patents identify output overvoltage limiting for all power devices, and overvoltage limit protection is provided for power devices by using proportionately scaled zeners to monitor and track the output off voltage of each device to prevent power device failure. The zener device is circuit configured such that it provides feedback to the gate of the power device. When zener avalanche occurs the power device partially turns on, absorbing the excess overvoltage energy in conjunction with the connective load.

Reference can also be had to U.S. Pat. No. 4,646,222 for disclosing an inverter incorporating overvoltage clamping. Overvoltage clamping is provided by using diode clamping devices referenced to DC power sources. The DC power sources provide a predetermined reference voltage to clamp the overvoltage condition, absorbing the excess energy through clamp diodes which dissipate the excess voltage in the form of heat.

It would be advantageous as to provide an electrosurgical generator having improved overvoltage limit and transient energy suppression.

SUMMARY

The foregoing and other problems are overcome by methods and apparatus in accordance with embodiments disclosed herein.

An electrosurgical generator includes a controlling data processor that executes software algorithms providing a number of new and useful features. These features preferably include the generation of an initial pulse, that is a low power pulse of RF energy that is used to sense at least one electrical characteristic of the tissue prior to starting an electrosurgical desiccation cycle, such as a tissue sealing cycle. The sensed electrical characteristic is then used as an input into the determination of initial sealing parameters, thereby making the sealing procedure adaptive to the characteristics of the tissue to be sealed. Another feature preferably provided measures the time required for the tissue to begin desiccating, preferably by observing an electrical transient at the beginning of an RF energy pulse, to determine and/or modify further seal parameters. Another preferable feature performs a tissue temperature control function by adjusting the duty cycle of the RF energy pulses applied to the tissue, thereby avoiding the problems that can result from excessive tissue heating. A further preferable feature controllably decreases the RF pulse voltage with each pulse of RF energy so that as the tissue desiccates and shrinks (thereby reducing the spacing between the surgical tool electrodes), arcing between the electrodes is avoided, as is the tissue destruction that may result from uncontrolled arcing. Preferably a Seal Intensity operator control is provided that enables the operator to control the sealing of tissue by varying parameters other than simply the RF power.

The system disclosed herein preferably further provides a unique method for overvoltage limiting and transient energy suppression. An electrosurgical system uses dynamic, real-time automatic detuning of the RF energy delivered to the tissue of interest. More specifically, this technique automatically limits excess output RF voltages by dynamically changing the tuning in a resonant source of RF electrosurgical energy, and by altering the shape of the RF source signal used to develop the output RF signal. The inventive technique limits the excess output transient RF energy by a resonant detuning of the generator. This occurs in a manner which does not clip or significantly distort the generated RF output signal used in a clinical environment for electrosurgical applications.

A method for electrosurgically sealing a tissue, in accordance with this disclosure, preferably includes the steps of (A) applying an initial pulse of RF energy to the tissue, the pulse having characteristics selected so as not to appreciably heat the tissue; (B) measuring a value of at least one electrical characteristic of the tissue in response to the applied first pulse; (C) in accordance with the measured at least one electrical characteristic, determining an initial set of pulse parameters for use during a first RF energy pulse that is applied to the tissue; and (D) varying the pulse parameters of subsequent RF energy pulses individually in accordance with at least one characteristic of an electrical transient that occurs at the beginning of each individual subsequent RF energy pulse. The method terminates the generation of subsequent RF energy pulses based upon a reduction in the output voltage or upon a determination that the electrical transient is absent.

The at least one characteristic that controls the variation of the pulse parameters is preferably a width of the electrical transient that occurs at the beginning of each subsequent RF energy pulse. The initial set of pulse parameters include a magnitude of a starting power and a magnitude of a starting voltage, and the pulse parameters that are varied include a pulse duty cycle and a pulse amplitude. Preferably, the subsequent RF energy pulses are each reduced in amplitude by a controlled amount from a previous RF energy pulse, thereby compensating for a decrease in the spacing between the surgical tool electrodes due to desiccation of the tissue between the electrodes.

The step of determining an initial set of pulse parameters preferably includes a step of using the measured value of at least one electrical characteristic of the tissue to readout the initial set of pulse parameters from an entry in a lookup table.

The step of determining an initial set of pulse parameters may also preferably include a step of reading out the initial set of pulse parameters from an entry in one of a plurality of lookup tables, where the lookup table is selected either manually or automatically, based on the electrosurgical instrument or tool that is being used.

The method also preferably includes a step of modifying predetermined ones of the pulse parameters in accordance with a control input from an operator. The predetermined ones of the pulse parameters that are modified include a pulse power, a pulse starting voltage level, a pulse voltage decay scale factor, and a pulse dwell time.

Preferably a circuit is coupled to the output of the electrosurgical generator for protecting the output against an overvoltage condition, and includes a suppressor that detunes a tuned resonant circuit at the output for reducing a magnitude of a voltage appearing at the output. In accordance with this aspect of the disclosure, the circuit has a capacitance network in parallel with an inductance that forms a portion of the output stage of the generator. A voltage actuated switch, such as a transorb, couples an additional capacitance across the network upon an occurrence of an overvoltage condition, thereby detuning the resonant network and reducing the magnitude of the voltage output.

BRIEF DESCRIPTION OF THE DRAWINGS

The above set forth and other features of the invention are made more apparent in the ensuing Detailed Description when read in conjunction with the attached Drawings, wherein:

FIG. 6A is a simplified block diagram of a presently preferred embodiment of the power control circuit of the electrosurgical generator of FIG. 2;

FIG. 6B depicts the organization of a seal parameter lookup table (LUT) shown in FIG. 6A;

FIG. 8 depicts a full set of electrosurgical RF pulses in accordance with this disclosure, and illustrates the voltage, current and power characteristics of the pulses, as well as the response of the tissue impedance to the applied RF pulses;

FIG. 9A illustrates a Seal Intensity control that forms a part of this disclosure, while FIGS. 9B and 9C show a preferred variation in certain parameters from the seal parameter LUT based on different Seal Intensity settings;

DETAILED DESCRIPTION OF THE PREFERRED EMBODIMENT

Figure 1A:
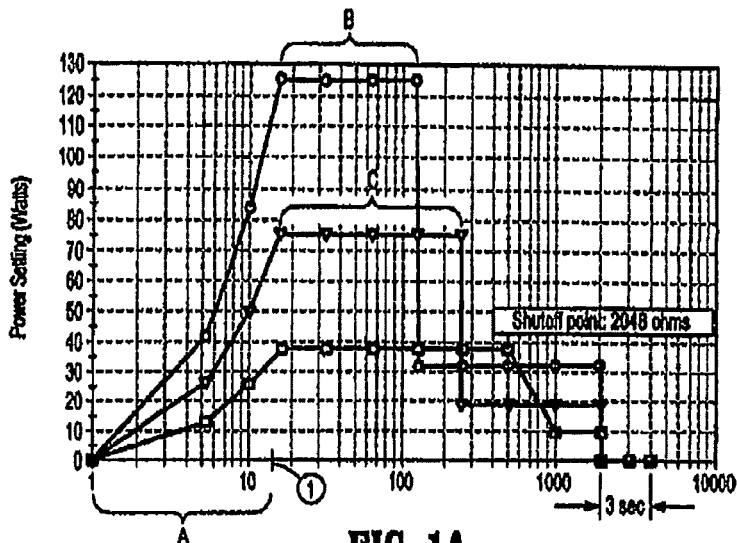
FIG. 1A is a graph that plots output power versus tissue impedance (Z) in ohms, in accordance with the operation of a prior art electrosurgical generator.
Figure 2:
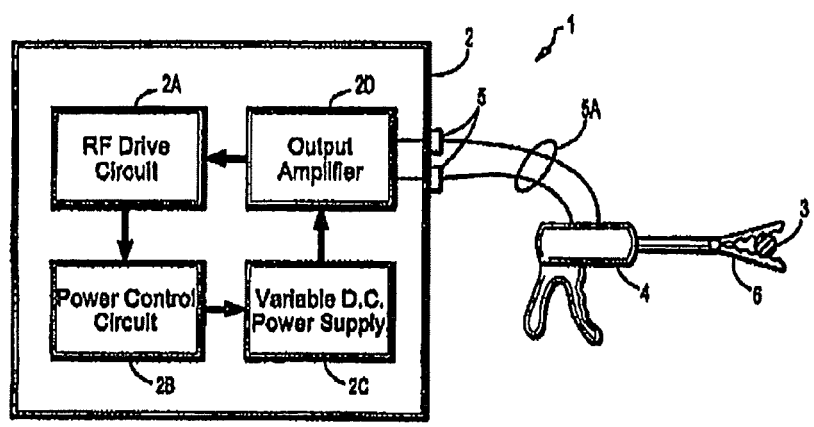
FIG. 2 is a simplified block diagram of an electrosurgical system that can be used to practice the teachings of this disclosure.

An electrosurgical system 1, which can be used to practice this invention, is shown in FIG. 2. The system 1 can be used for sealing vessels 3 and other tissues of a patient, including ducts, veins, arteries and vascular tissue. The system 1 includes an electro-surgical generator 2 and a surgical tool, also referred to herein as a surgical instrument 4. The surgical instrument 4 is illustrated by way of example, and as will become apparent from the discussion below, other instruments can be utilized. The electrosurgical generator 2, which is of most interest to the teachings herein, includes several interconnected sub-units, including an RF drive circuit 2A, a power control circuit 2B, a variable D.C. power supply 2C and an output amplifier 2D. The surgical instrument 4 is electrically connected to the electrosurgical generator 2 using a plug 5 for receiving controlled electrosurgical power therefrom. The surgical instrument 4 has some type of end effector member 6, such as a forceps or hemostat, capable of grasping and holding the vessels and tissues of the patient. The member 6, also referred to simply as end effector 6, is assumed, in this embodiment, to be capable of applying and maintaining a relatively constant level of pressure on the vessel 3.

The member 6 is provided in the form of bipolar electrosurgical forceps using two generally opposing electrodes disposed on inner opposing surfaces of the member 6, and which are both electrically coupled to the output of the electrosurgical generator 2. During use, different electric potentials are applied to each electrode. In that tissue is an electrical conductor, when the forceps are utilized to clamp or grasp the vessel 3 therebetween, the electrical energy output from the electrosurgical generator 2 is transferred through the intervening tissue. Both open surgical procedures and endoscopic surgical procedures can be performed with suitably adapted surgical instruments 4. It should also be noted that the member 6 could be monopolar forceps that utilize one active electrode, with the other (return) electrode or pad being attached externally to the patient, or a combination of bipolar and monopolar forceps.

Figure 3:
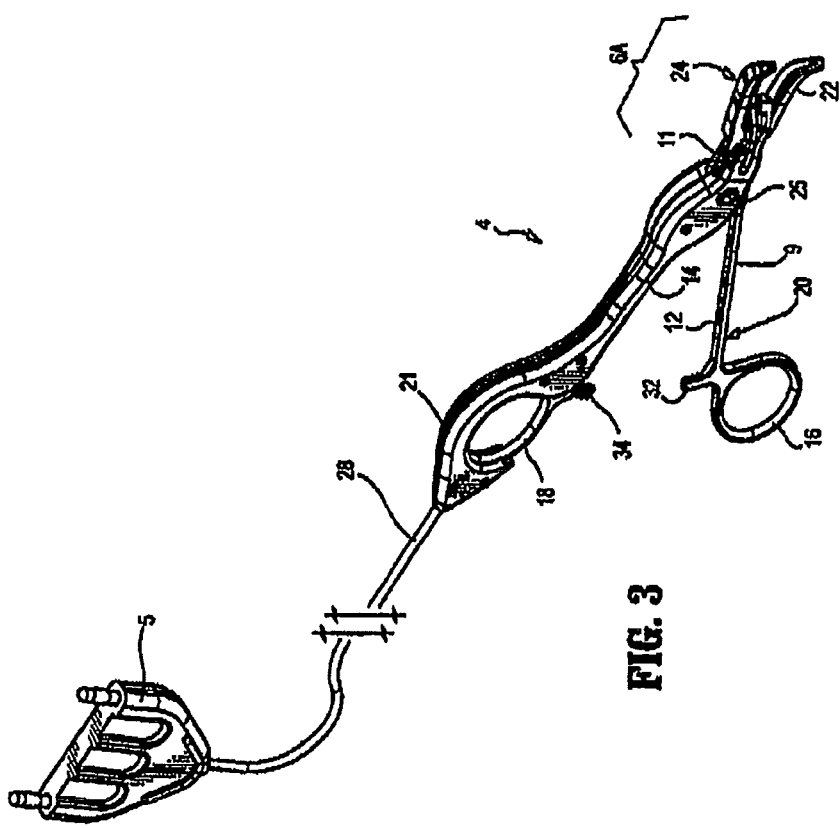
FIG. 3 is a perspective view of one embodiment of a surgical instrument having bipolar forceps that are suitable for practicing this disclosure.
Figure 4:
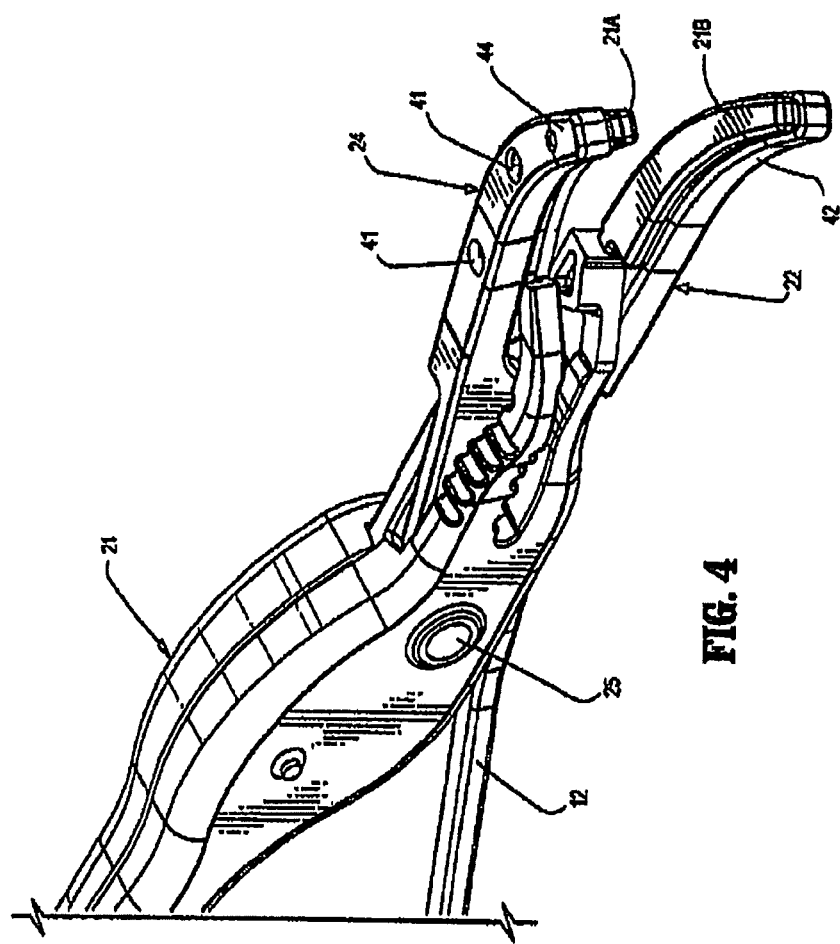
FIG. 4 is an enlarged, perspective view of a distal end of the bipolar forceps shown in FIG. 3.

By way of further explanation, FIG. 3 is a perspective view of one embodiment of the surgical instrument 4 having a bipolar end effector implemented as forceps 6A while FIG. 4 is an enlarged, perspective view of a distal end of the bipolar forceps 6A shown in FIG. 3.

Referring now to FIGS. 3 and 4, a bipolar surgical instrument 4 for use with open surgical procedures includes a mechanical forceps 20 and an electrode assembly 21. In the drawings and in the description which follows, the term "proximal", as is traditional, refers to the end of the instrument 4 which is closer to the user, while the term "distal" refers to the end which is further from the user.

Mechanical forceps 20 includes first and second members 9 and 11 which each have an elongated shaft 12 and 14, respectively. Shafts 12 and 14 each include a proximal end and a distal end. Each proximal end of each shaft portion 12, 14 includes a handle member 16 and 18 attached thereto to allow a user to effect movement of the two shaft portions 12 and 14 relative to one another. Extending from the distal end of each shaft portion 12 and 14 are end effectors 22 and 24, respectively. The end effectors 22 and 24 are movable relative to one another in response to movement of handle members 16 and 18. These end effectors members 6A can be referred to collectively as bipolar forceps.

Preferably, shaft portions 12 and 14 are affixed to one another at a point proximate the end effectors 22 and 24 about a pivot 25. As such, movement of the handles 16 and 18 imparts movement of the end effectors 22 and 24 from an open position, wherein the end effectors 22 and 24 are disposed in spaced relation relative to one another, to a clamping or closed position, wherein the end effectors 22 and 24 cooperate to grasp the tubular vessel 3 therebetween. Either one or both of the end effectors 22, 24 can be movable.

As is best seen in FIG. 4, end effector 24 includes an upper or first jaw member 44 which has an inner facing surface and a plurality of mechanical interfaces disposed thereon which are dimensioned to releasable engage a portion of an electrode assembly 21, which may be disposable. Preferably, the mechanical interfaces include sockets 41 which are disposed at least partially through the inner facing surface of jaw member 44 and which are dimensioned to receive a complimentary detent attached to an upper electrode 21A of the disposable electrode assembly 21. The upper electrode 21A is disposed across from a corresponding lower electrode 21B. The end effector 22 includes a second or lower jaw member 42 which has an inner facing surface which opposes the inner facing surface of the first jaw member 44.

Preferably, shaft members 12 and 14 of the mechanical forceps 20 are designed to transmit a particular desired force to the opposing inner facing surfaces of the jaw members 22 and 24 when clamped. In particular, since the shaft members 12 and 14 effectively act together in a spring-like manner (i.e., bending that behaves like a spring), the length, width, height and deflection of the shaft members 12 and 14 directly impacts the overall transmitted force imposed on opposing jaw members 42 and 44. Preferably, jaw members 22 and 24 are more rigid than the shaft members 12 and 14 and the strain energy stored in the shaft members 12 and 14 provides a constant closure force between the jaw members 42 and 44.

Each shaft member 12 and 14 also includes a ratchet portion 32 and 34. Preferably, each ratchet, e.g., 32, extends from the proximal end of its respective shaft member 12 towards the other ratchet 34 in a generally vertically aligned manner such that the inner facing surfaces of each ratchet 32 and 34 abut one another when the end effectors 22 and 24 are moved from the open position to the closed position. Each ratchet 32 and 34 includes a plurality of flanges which project from the inner facing surface of each ratchet 32 and 34 such that the ratchets 32 and 34 can interlock in at least one position. In the embodiment shown in FIG. 3, the ratchets 32 and 34 interlock at several different positions. Preferably, each ratchet position holds a specific, i.e., constant, strain energy in the shaft members 12 and 14 which, in turn, transmits a specific force to the end effectors 22 and 24 and, thus, to the electrodes 21A and 21B. Also, preferably a stop is provided on one or both of the end effectors 22, 24 to maintain a preferred gap between the jaws.

In some cases it may be preferable to include other mechanisms to control and/or limit the movement of the jaw members 42 and 44 relative to one another. For example, a ratchet and pawl system could be utilized to segment the movement of the two handles into discrete units which, in turn, impart discrete movement to the jaw members 42 and 44 relative to one another.

Figure 5:
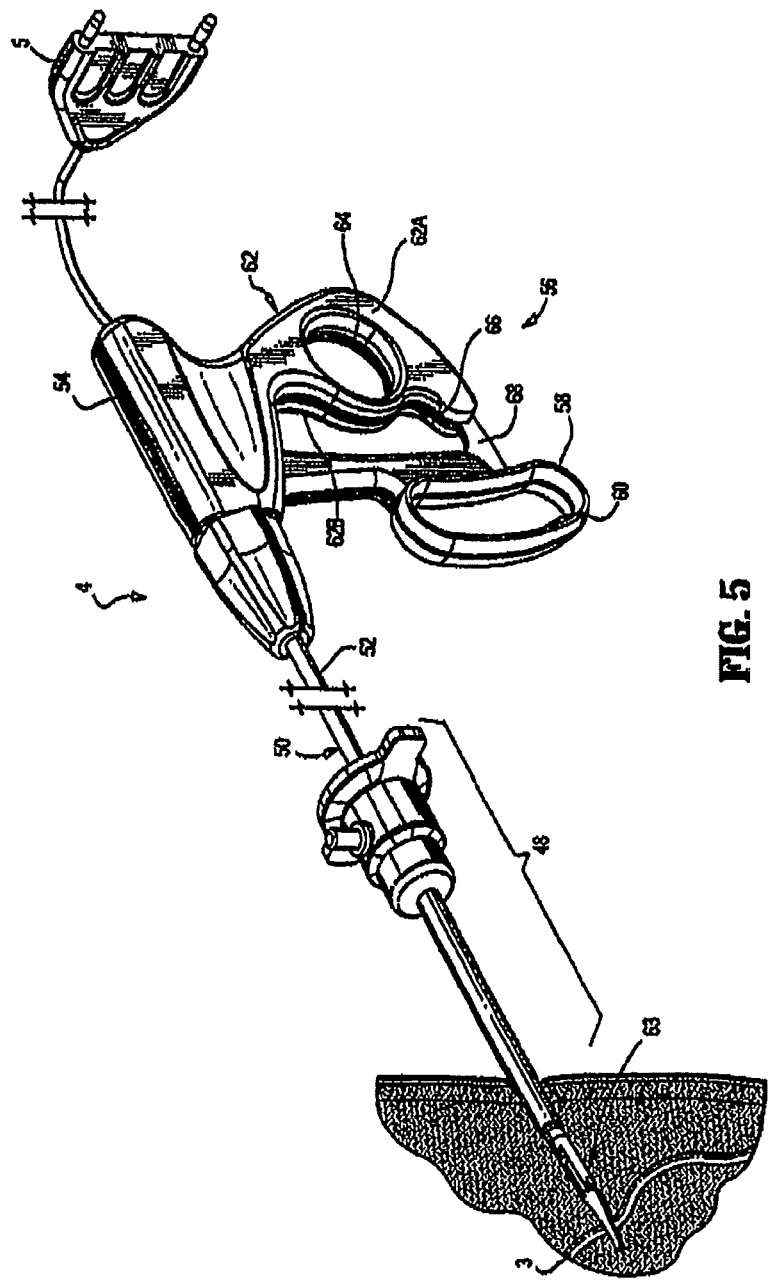
FIG. 5 is a perspective view of an embodiment of a surgical instrument having forceps that are suitable for use in an endoscopic surgical procedure utilizing the electrosurgical system disclosed herein.

FIG. 5 is a perspective view of an embodiment of the surgical instrument 4 having end effector members or forceps 63 that are suitable for an endoscopic surgical procedure. The end effector member 63 is depicted as sealing the tubular vessel 3 through a cannula assembly 48.

The surgical instrument 4 for use with endoscopic surgical procedures includes a drive rod assembly 50 which is coupled to a handle assembly 54. The drive rod assembly 50 includes an elongated hollow shaft portion 52 having a proximal end and a distal end. An end effector assembly 63 is attached to the distal end of shaft 52 and includes a pair of opposing jaw members. Preferably, handle assembly 54 is attached to the proximal end of shaft 52 and includes an activator 56 for imparting movement of the forceps jaw members of end effector member 63 from an open position, wherein the jaw members are disposed in spaced relation relative to one another, to a clamping or closed position, wherein the jaw members cooperate to grasp tissue therebetween.

Activator 56 includes a movable handle 58 having an aperture 60 defined therein for receiving at least one of the operator's fingers and a fixed handle 62 having an aperture 64 defined therein for receiving an operator's thumb. Movable handle 58 is selectively moveable from a first position relative to fixed handle 62 to a second position in the fixed handle 62 to close the jaw members. Preferably, fixed handle 62 includes a channel 66 which extends proximally for receiving a ratchet 68 which is coupled to movable handle 58. This structure allows for progressive closure of the end effector assembly, as well as a locking engagement of the opposing jaw members. In some cases it may be preferable to include other mechanisms to control and/or limit the movement of handle 58 relative to handle 62 such as, e.g., hydraulic, semi-hydraulic and/or gearing systems. As with instrument 4, a stop can also be provided to maintain a preferred gap between the jaw members.

The handle 62 includes handle sections 62a and 62b, and is generally hollow such that a cavity is formed therein for housing various internal components. For example, the cavity can house a PC board which connects the electrosurgical energy being transmitted from the electrosurgical generator 2 to each jaw member, via connector 5. More particularly, electrosurgical energy generated from the electrosurgical generator 2 is transmitted to the handle PC board by a cable 5A. The PC board diverts the electrosurgical energy from the generator into two different electrical potentials which are transmitted to each jaw member by a separate terminal clip. The handle 62 may also house circuitry that communicates with the generator 2, for example, identifying characteristics of the electrosurgical tool 4 for use by the electrosurgical generator 2, where the electrosurgical generator 2 may select a particular seal parameter lookup table based on those characteristics (as described below).

Preferably, a lost motion mechanism is positioned between each of the handle sections 62a and 62b for maintaining a predetermined or maximum clamping force for sealing tissue between the jaw members.

Having thus described two exemplary and non-limiting embodiments of surgical instruments 4 that can be employed with the electrosurgical generator 2, a description will now be provided of various aspects of the inventive electrosurgical generator 2.

FIG. 6A is a block diagram that illustrates the power control circuit 2B of FIG. 2 in greater detail. The power control circuit 2B includes a suitably programmed data processor 70 that is preferably implemented as one or more microcontroller devices. In a most preferred embodiment there are two principal microcontrollers, referred to as a main microcontroller 70A and a feedback microcontroller 70B. These two microcontrollers are capable of communicating using shared data that is stored and retrieved from a shared read/write memory 72. A control program for the data processor 70 is stored in a program memory 74, and includes software routines and algorithms for controlling the overall operation of the electrosurgical generator 2. In general, the feedback microcontroller 70B has a digital output bus coupled to an input of a digital to analog converter (DAC) block 76 which outputs an analog signal. This is a system control voltage (SCV), which is applied to the variable DC power supply 2C to control the magnitude of the voltage and current of output RF pulses.

An analog to digital converter (ADC) block 78 receives analog inputs and sources a digital input bus of the feedback microcontroller 70B. Using the ADC block 78 the microcontroller 70B is apprised of the value of the actual output voltage and the actual output current, thereby closing the feedback loop with the SCV signal. The values of the output voltage and current can be used for determining tissue impedance, power and energy delivery for the overall, general control of the applied RF energy waveform. It should be noted that at least the ADC block 78 can be an internal block of the feedback microcontroller 70B, and need not be a separate, external component. It should be further noted that the same analog signals can be digitized and read into the master microcontroller 70A, thereby providing redundancy. The master microcontroller 70A controls the state (on/off) of the high voltage (e.g., 190V max) power supply as a safety precaution, controls the front panel display(s), such as a Seal Intensity display, described below and shown in FIG. 9A, and also receives various input switch closures, such as a Seal Intensity selected by an operator.

It is noted that in a preferred embodiment of the electrosurgical generator 2 a third (waveform) microcontroller 70C is employed to generate the desired 470 kHz sinusoidal waveform that forms the basis of the RF pulses applied to the tissue to be sealed, such as the vessel 3 (FIG. 2). The waveform microcontroller 70C is controlled by the feedback microcontroller 70B and is programmed thereby. An output signal line from the feedback microcontroller 70B is coupled to a Reset input of the waveform microcontroller 70C to essentially turn the waveform microcontroller 70C on and off to provide the pulsed RF signal in accordance with an aspect of this disclosure. This particular arrangement is, of course, not to be viewed in a limiting sense upon the practice of this system, as those skilled in the art may derive a number of methods and circuits for generating the desired RF pulses in accordance with the teachings found herein.

As an overview, the software algorithms executed by the data processor 70 provide the following features. First, and referring now also to the preferred waveform depicted in FIGS. 7A and 7B, a low power initial pulse of RF energy is used to sense at least one electrical characteristic of the tissue prior to starting the seal cycle. Second, the sensed electrical characteristic of the tissue is used as an input into the determination of the initial sealing parameters, thereby making the sealing procedure adaptive to the characteristics of the tissue to be sealed. Third, the technique measures the time required for the tissue to begin desiccating, preferably by observing an electrical transient, to determine and/or modify further seal parameters. Fourth, the technique performs a tissue temperature control function by adjusting the duty cycle of RF pulses applied to the tissue, thereby avoiding excessive tissue heating and the problems that arise from excessive tissue heating. This is preferably accomplished by using at least one calculated seal parameter related to the time required for the tissue to begin desiccating. Fifth, the technique controllably changes the RF pulse voltage with each pulse of RF energy DEL as the tissue desiccates and shrinks (thereby reducing the pacing between the surgical instrument electrodes), arcing between the instrument electrodes (e.g. 21A and 21B of FIG. 4) is avoided, as is the tissue destruction that may result from such uncontrolled arcing This is also preferably accomplished by using at least one calculated seal parameter that is related to the time required for the tissue to begin desiccating. Sixth, the above-mentioned Seal Intensity front panel control (FIG. 9A) enables the operator to control the sealing of tissue by varying parameters other than simply the RF power. These various aspects of this disclosure are now described in further detail.

Figure 13:
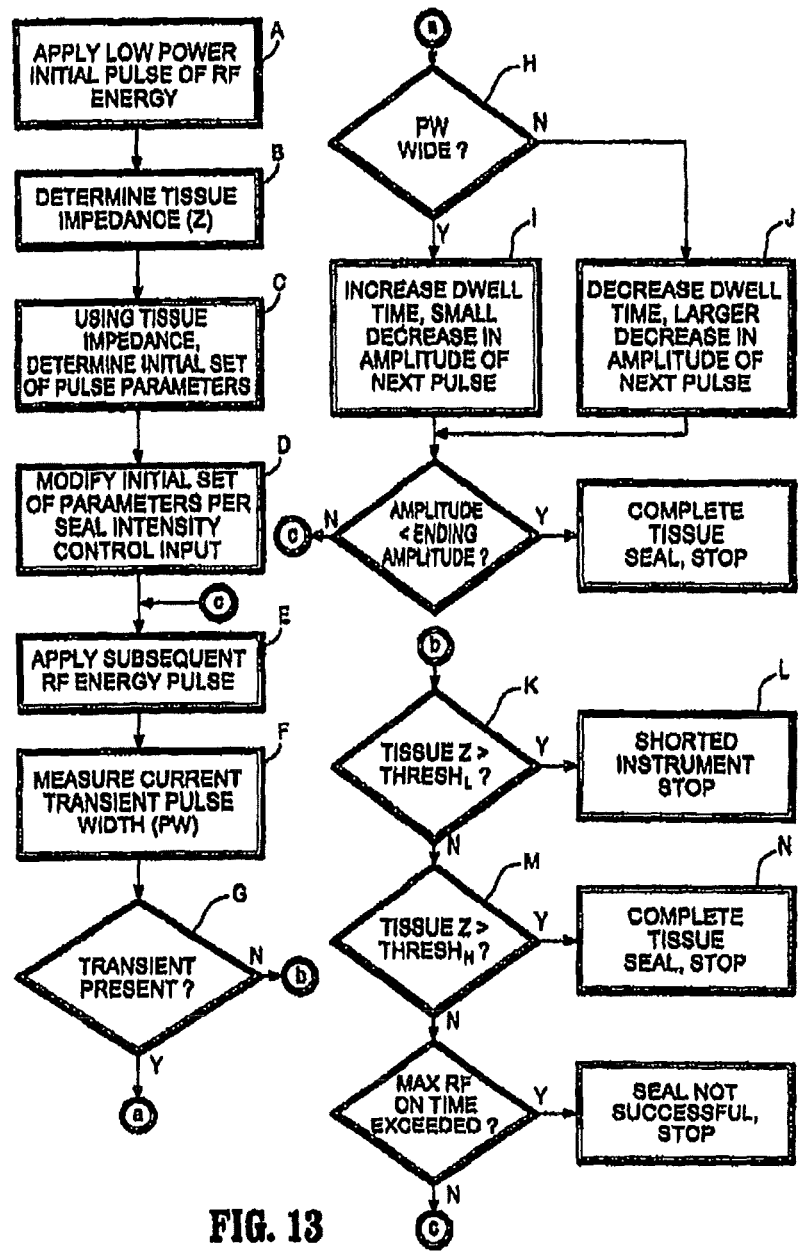
FIG. 13 is a more detailed logic flow diagram that illustrates a method in accordance with the system disclosed herein.

Referring now also to the logic flow diagram of FIG. 13, the impedance sensing feature is implemented at the beginning of the seal cycle, wherein the electrosurgical generator 2 senses at least one electrical characteristic of the tissue, for example, impedance, I-V phase rotation, or the output current, by using a short burst of RF energy (FIG. 13, Steps A and B). The electrical characteristic of the tissue may be measured at any frequency or power level, but preferably is performed at the same frequency as the intended working frequency (e.g., 470 kHz). In a most preferred case the short burst of RF energy (preferably less than about 200 millisecond, and more preferably about 100 millisecond) is a 470 kHz sine wave with approximately 5 W of power. The initial pulse RF power is made low, and the pulse time is made as short as possible, to enable an initial tissue electrical characteristic measurement to be made without excessively heating the tissue.

In a most preferred embodiment the electrical characteristic sensed is the tissue impedance which is employed to determine an initial set of parameters that are input to the sealing algorithm, and which are used to control the selection of sealing parameters, including the starting power, current and voltage (FIG. 13, Step C). Other sealing parameters may include duty cycle and pulse width. Generally, if the sensed impedance is in the lower ranges, then the initial power and starting voltage are made relatively lower, the assumption being that the tissue will desiccate faster and require less energy. If the sensed impedance is in the higher ranges, the initial power and starting voltage are made relatively higher, the assumption being that the tissue will desiccate slower and require more energy.

In other embodiments at least one of any other tissue electrical characteristic, for example, the voltage or current, can be used to set the parameters. These initial parameters are preferably modified in accordance with the setting of the Seal Intensity control input (FIG. 13, Step D), as will be described in further detail below.

Referring again to FIG. 13, Step C, the sensed impedance is employed to determine which set of values are used from a seal parameter lookup table (LUT) 80 (see FIGS. 6A and 6B). The seal parameter look up table may one of a plurality that are stored in the generator or accessible to the generator. Furthermore, the seal parameter table may be selected manually or automatically, based on, for example, the electrosurgical tool or instrument being employed. The specific values read from the seal parameter LUT 80 (FIG. 6B) are then adjusted based on the Seal Intensity front panel setting 82 (FIG. 13, Step D), as is shown more clearly in FIGS. 9A and 9B. In a preferred, but not limiting embodiment, the values read from the seal parameter LUT 80 comprise the power, the maximum voltage, starting voltage, minimum voltage, voltage decay, voltage ramp, maximum RF on time, maximum cool scale factor, pulse minimum, pulse dwell time, pulse off time, current and the desired pulse width. In a preferred, but not limiting embodiment, the seal parameter values adjusted by the Seal Intensity front panel setting 82 (FIGS. 9A and 9B) comprise the power, starting voltage, voltage decay, and pulse dwell time.

Figure 1B:
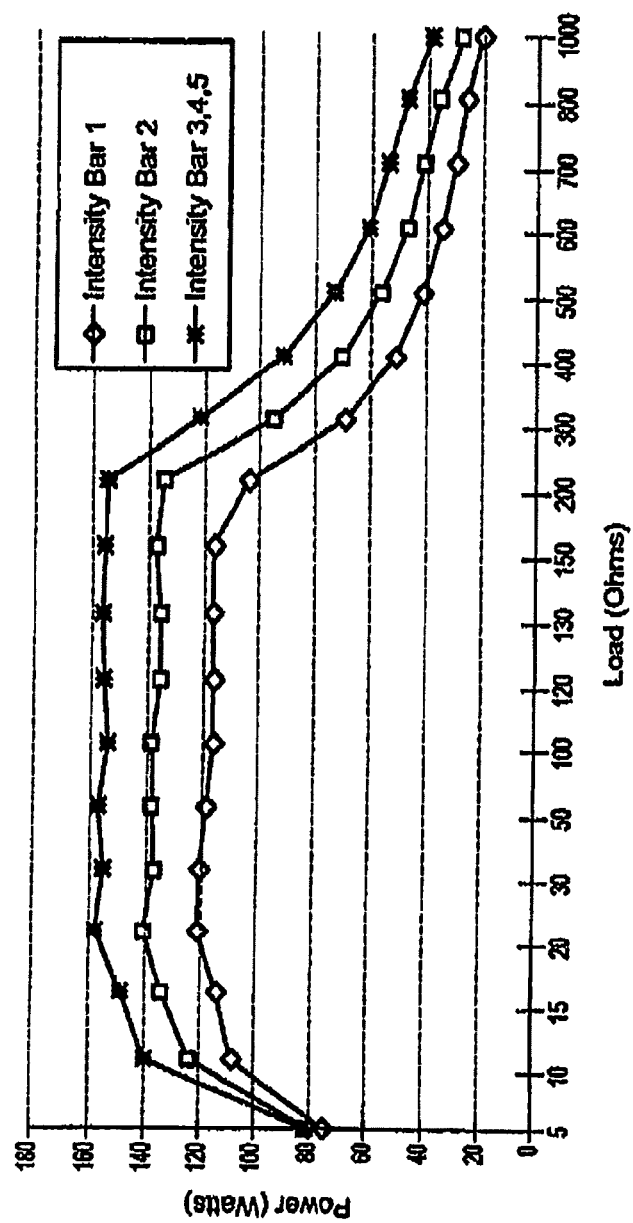
FIG. 1B is a graph that plots output power versus impedance in ohms, in accordance with the operation of an electrosurgical generator that is an aspect of this disclosure.

FIG. 1B is a graph that plots output power versus impedance in ohms for the disclosed electrosurgical generator. The plot labeled "Intensity Bar 1" shows the electrosurgical generator power output versus impedance when the "VLOW" setting 82A (FIG. 9A) of the Seal Intensity front panel setting 82 is selected. The plot labeled Intensity Bar 2 shows the power output of the electrosurgical generator when the "LOW" setting 82B of the Seal Intensity front panel setting 82 is selected. The plot labeled Intensity Bars 3, 4, 5, shows the power output of the electrosurgical generator when the "MED" 82C, "HIGH" 82D or "VHIGH" 82E Seal Intensity front panel settings 82 are selected. The Seal Intensity front panel settings 82 adjust the seal parameter values as shown in FIG. 9B. These values may be adjusted depending on instrument used, tissue characteristics or surgical intent.

Figure 7A:
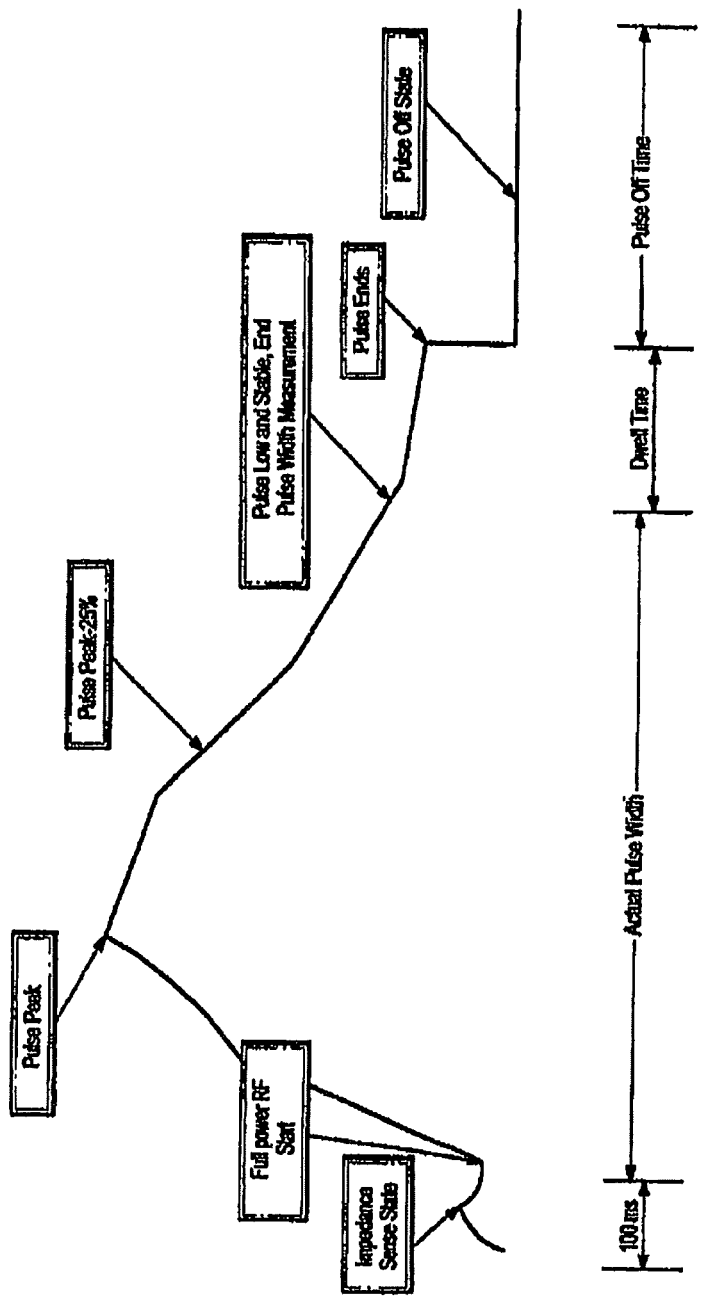
FIGS. 7A and 7B illustrate a presently preferred electrosurgical generator output waveform of RMS current vs. time for implementing at least the first pulse of the pulsed operation mode that is an aspect of this disclosure.
Figure 7B:
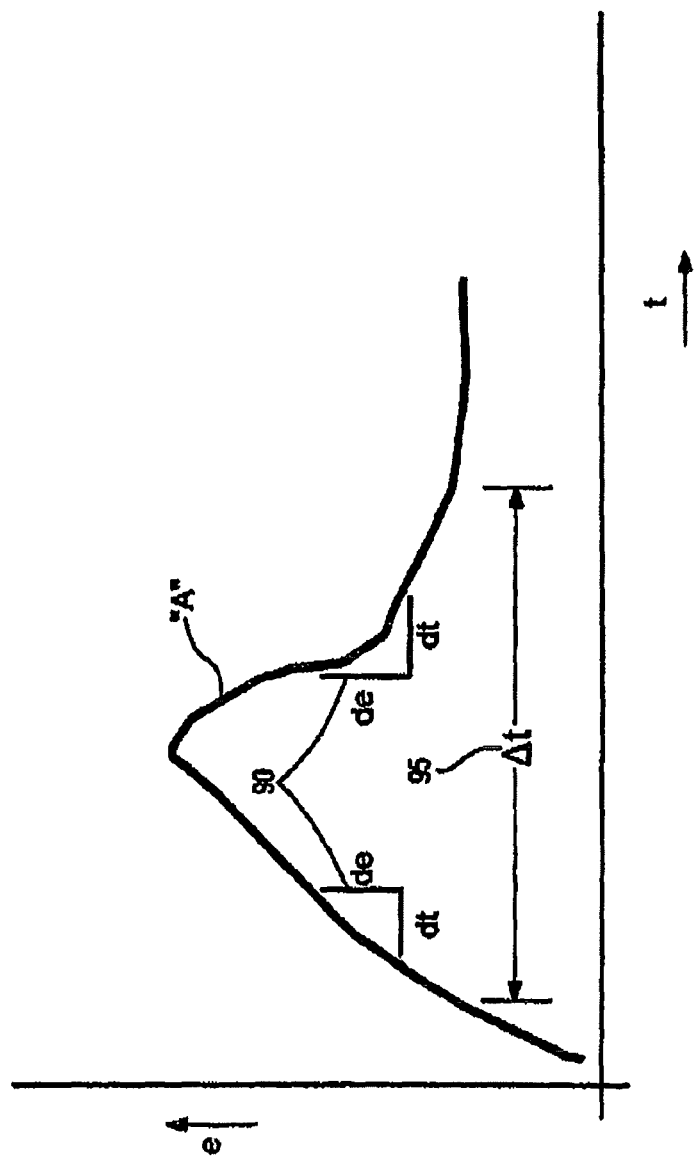

Discussing this aspect of the disclosure now in further detail, and referring as well to FIGS. 7A, 7B and 8, the selected Seal Parameter Table, adjusted by the Seal Intensity front panel settings is then utilized by the RF energy generation system and an initial RF sealing pulse is then started.

As each pulse of RF energy is applied to the tissue, the current initially rises to a maximum (Pulse Peak) and then, as the tissue desiccates and the impedance rises due to loss of moisture in the tissue, the current falls. Reference in this regard can be had to the circled areas designated as "A" in the $I_{rms}$ waveform of FIG. 8. The actual width of the resulting electrical transient, preferably a current transient "A", is an important factor in determining what type and amount of tissue is between the jaws (electrodes) of the surgical instrument 4 (measured from "Full Power RF Start" to "Pulse Low and Stable".) The actual current transient or pulse width is also employed to determine the changes to, or the values of, the parameters of the pulse duty cycle ("Dwell Time") and to the change of the pulse voltage, as well as other parameters. This parameter can also be used to determine whether the tissue seal has been completed, or if the surgical instrument 4 has shorted.

As an alternative to directly measuring the pulse width, the rate of change of an electrical characteristic (for example current, voltage, impedance, etc.) of the transient "A" (shown in FIG. 7B) may be measured periodically (indicated by the reference number 90 shown in FIG. 7B) over the time the transient occurs. The rate of change of the electrical characteristic may be proportional to the width, Δt 95 of the transient "A", defined by the relationship:

$$\Delta t \approx de/dt$$

where de/dt is the change in the electrical characteristic over time. This rate of change may then be used to provide an indication of the width of the transient "A" in determining the type and amount of tissue that is between the jaws (electrodes) of the surgical instrument 4, as well as the subsequent pulse duty cycle ("Dwell Time"), the amount of subsequent pulse voltage reduction, as well as other parameters.

Referring to FIG. 13, Step E, a subsequent RF energy pulse is applied to the tissue, and the pulse width of the leading edge current transient is measured (FIG. 13, Step F). A determination is made if the current transient is present. If it is, control passes via connector "a" to Step H, otherwise control passes via connector "b" to Step K.

Assuming that the current transient is present, and referring to FIG. 13, Step H, if the current transient pulse is wide, for example, approximately in the range of 500-1000 ms, then one can assume the presence of a large amount of tissue, or tissue that requires more RF energy to desiccate. Thus, the Dwell Time is increased, and an increase or small reduction is made in the amplitude of the next RF pulse (see the Vrms waveform in FIG. 8, and FIG. 13, Step I). If the current transient pulse is narrow, for example, about 250 ms or less (indicating that the tissue impedance rapidly rose), then one can assume a small amount of tissue, or a tissue type that requires little RF energy to desiccate is present. Other ranges of current transient pulse widths can also be used. The relationship between the current transient pulse width and the tissue characteristics may be empirically derived. In this case the Dwell Time can be made shorter, and a larger reduction in the amplitude of the next RF pulse can be made as well (FIG. 13, Step J).

If a current pulse is not observed at FIG. 13, Step G, it may be assumed that either the instrument 4 has shorted, the tissue has not yet begun to desiccate, or that the tissue has been fully desiccated and, thus, the seal cycle is complete. The determination of which of the above has occurred is preferably made by observing the tissue impedance at FIG. 13, Steps K and M. If the impedance is less than a low threshold value (THRESH$_L$), then a shorted instrument 4 is assumed (FIG. 13, Step L), while if the impedance is greater than a high threshold value (THRESH$_H$), then a complete tissue seal is assumed (FIG. 13, Step N).

If the tissue impedance is otherwise found to be between the high and low threshold values, a determination is made as to whether the Max RF On Time has been exceeded. If the Max RF On Time has been exceeded, it is assumed that the seal cannot be successfully completed for some reason and the sealing procedure is terminated. If the Max RF On Time has not been exceeded then it is assumed that the tissue has not yet received enough RF energy to start desiccation, and the seal cycle continues (connector "c").

After the actual pulse width measurement has been completed, the Dwell Time is determined based on the actual pulse width and on the Dwell Time field in the seal parameter LUT 80 (see FIG. 6B.) The RF pulse is continued until the Dwell Time has elapsed, effectively determining the total time that RF energy is delivered for that pulse. The RF pulse is then turned off or reduced to a very low level for an amount of time specified by the Pulse Off field. This low level allows some moisture to return to the tissue.

Based on the initial Desired Pulse Width field of the seal parameter LUT 80 for the first pulse, or, for subsequent pulses, the actual pulse width of the previous pulse, the desired voltage limit kept constant or adjusted based on the Voltage Decay and Voltage Ramp fields. The desired voltage limit is kept constant or raised during the pulse if the actual pulse width is greater than the Desired Pulse Width field (or last actual) pulse width), and is kept constant or lowered if the actual pulse width is less than the Desired Pulse Width field (or the last actual pulse width).

When the Desired Voltage has been reduced to the Minimum Voltage field, then the RF energy pulsing is terminated and the electrosurgical generator 2 enters a cool-down period having a duration that is set by the Maximum Cool SF field and the actual pulse width of the first pulse.

Several of the foregoing and other terms are defined with greater specificity as follows (see also FIGS. 7A and 7B).

The Actual Pulse width is the time from pulse start to pulse low. The Pulse Peak is the point where the current reaches a maximum value, and does not exceed this value for some predetermined period of time (measured in milliseconds). The peak value of the Pulse Peak can be reached until the Pulse Peak-X % value is reached, which is the point where the current has decreased to some predetermined determined percentage, X, of the value of Pulse Peak. Pulse Low is the point where the current reaches a low point, and does not go lower for another predetermined period of time. The value of the Maximum RF On Time or MAX Pulse Time is preferably preprogrammed to some value that cannot be readily changed. The RF pulse is terminated automatically if the Pulse Peak is reached but the Pulse Peak-X % value is not obtained with the duration set by the Maximum RF On Time field of the seal parameter LUT 80.

Referring to FIG. 6B, the seal parameter LUT 80 is employed by the feedback microcontroller 70B in determining how to set the various outputs that impact the RF output of the electrosurgical generator 2. The seal parameter LUT 80 is partitioned into a plurality of storage regions, each being associated with a particular measured initial impedance. More particularly, the Impedance Range defines a plurality of impedance breakpoints (in ohms) which are employed to determine which set of variables are to be used for a particular sealing cycle. The particular Impedance Range that is selected is based on the above described Impedance Sense State (FIGS. 7A and 7B) that is executed at the start of the seal cycle. The individual data fields of the seal parameter LUT 80 are defined as follows.

The actual values for the Impedance Ranges of Low, Med Low, Med High, or High, are preferably contained in one of a plurality of tables stored in the generator 2, or otherwise accessible to the generator 2. A specific table may be selected automatically, for example, based on signals received from the electrosurgical tool 4 being used, or by the operator indicating what electrosurgical tool is in use.

Power is the RF power setting to be used (in Watts). Max Voltage is the greatest value that the output voltage can achieve (e.g., range 0-about 190V). Start Voltage is the greatest value that the first pulse voltage can achieve (e.g., range 0-about 190V). Subsequent pulse voltage values are typically modified downwards from this value. The Minimum Voltage is the voltage endpoint, and the seal cycle can be assumed to be complete when the RF pulse voltage has been reduced to this value. The Voltage Decay scale factor is the rate (in volts) at which the desired voltage is lowered if the current Actual Pulse Width is less than the Desired Pulse Width. The Voltage Ramp scale factor is the rate at which the desired voltage will be increased if the Actual Pulse Width is greater than the Desired Pulse Width. The Maximum RF On Time is the maximum amount of time (e.g., about 5-20 seconds) that the RF power can be delivered, as described above. The Maximum Cool Down Time determines the generator cool down time, also as described above. Pulse Minimum establishes the minimum Desired Pulse Width value. It can be noted that for each RF pulse, the Desired Pulse Width is equal to the Actual Pulse Width from the previous pulse, or the Desired Pulse field if the first pulse. The Dwell Time scale factor was also discussed previously, and is the time (in milliseconds) that the RF pulse is continued after the current drops to the Pulse Low and Stable point (see FIGS. 7A and 7B). Pulse Off is the off time (in milliseconds) between RF pulses. Desired Pulse Width is a targeted pulse width and determines when the Desired Voltage (Vset) is raised, lowered or kept constant. If the Actual Pulse Width is less than the Desired Pulse Width, then Vset is decreased, while if the Actual Pulse Width is greater than the Desired Pulse Width, then Vset is increased. If the Actual Pulse Width is equal to the Desired Pulse Width, then Vset is kept constant. The Desired Pulse Width is used as the Desired Pulse Width for each sequential pulse. In general, a new Desired Pulse Width cannot be greater than a previous Desired Pulse Width, and cannot be less than Pulse Minimum.

By applying the series of RF pulses to the tissue, the surgical generator 2 effectively raises the tissue temperature to a certain level, and then maintains the temperature relatively constant. If the RF pulse width is too long, then the tissue may be excessively heated and may stick to the electrodes 21A, 21B of the surgical instrument 4, and/or an explosive vaporization of tissue fluid may damage the tissue, such as the vessel 3. If the RF pulse width is too narrow, then the tissue will not reach a temperature that is high enough to properly seal. As such, it can be appreciated that a proper balance of duty cycle to tissue type is important.

During the pulse off cycle that is made possible in accordance with the teachings herein, the tissue relaxes, thereby allowing the steam to exit without tissue destruction. The tissue responds by rehydrating, which in turn lowers the tissue impedance. The lower impedance allows the delivery of more current in the next pulse. This type of pulsed operation thus tends to regulate the tissue temperature so that the temperature does not rise to an undesirable level, while still performing the desired electrosurgical procedure, and may also allow more energy to be delivered, and thus achieving better desiccation.

As each RF pulse is delivered to the tissue, the tissue desiccates and shrinks due to pressure being applied by the jaws of the surgical instrument 4. The inventors have realized that if the voltage applied to the tissue is not reduced, then as the spacing between the jaws of the surgical instrument 4 is gradually reduced due to shrinking of the tissue, an undesirable arcing can develop which may vaporize the tissue, resulting in bleeding.

As is made evident in the $V_{RMS}$ trace of FIG. 8, and as was described above, the voltage of each successive RF pulse can be controllably decreased, thereby compensating for the desiccation-induced narrowing of the gap between the surgical instrument electrodes 21A and 21B. That is, the difference in electric potential between the electrodes is decreased as the gap between the electrodes decreases, thereby avoiding arcing.

As was noted previously, the Seal Intensity front panel adjustment is not a simple RF power control. The adjustment of the seal intensity is accomplished by adjusting the power of the electrosurgical generator 2, as well as the generator voltage, the duty cycle of the RF pulses, the length of time of the seal cycle (e.g., number of RF pulses), and the rate of voltage reduction for successive RF pulses. FIGS. 9B and 9C illustrate an exemplary set of parameters (Power, Start Voltage, Voltage Decay and Dwell Time), and how they modify the contents of the seal parameter LUT 80 depending on the setting of the Seal Intensity control 82 shown in FIG. 9A. Generally, higher settings of the Seal Intensity control 82 increase the seal time and the energy delivered while lower settings decrease the seal time and the energy delivered.

In the FIG. 9B embodiment, it is instinctive to note that for the Medium, High and Very High Seal Intensity settings the RF Power remains unchanged, while variations are made instead in the Start Voltage, Voltage Decay and Dwell Time parameters.

Figure 12:
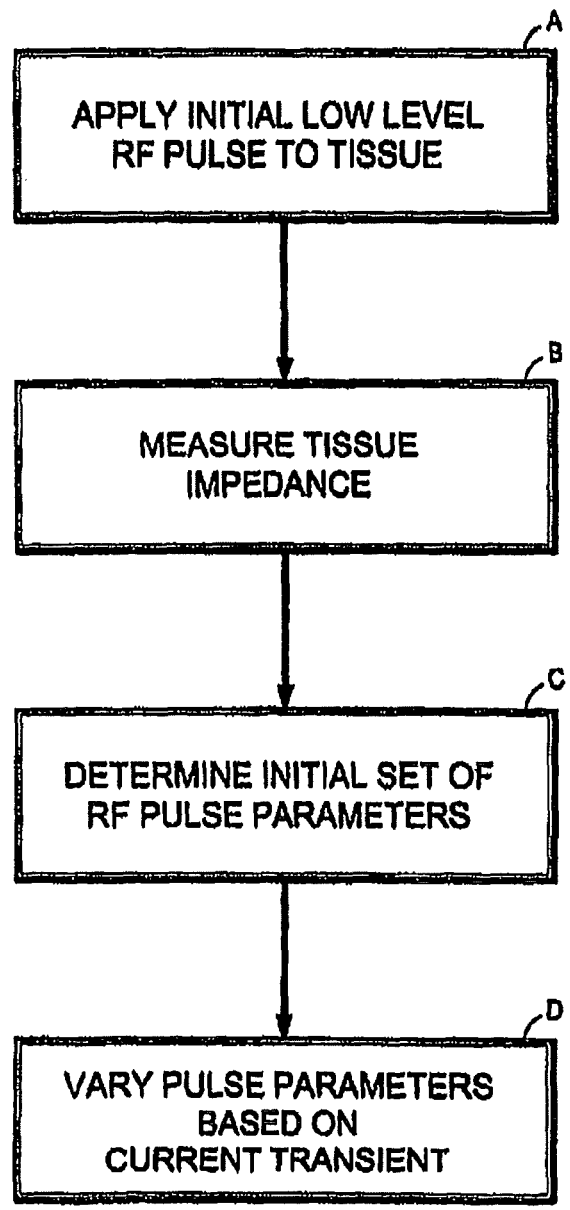
FIG. 12 is a logic flow diagram that illustrates a method in accordance with the system disclosed herein.

Based on the foregoing it can be appreciated that an aspect of this disclosure is a method for electrosurgically sealing a tissue. Referring to FIG. 12, the method includes steps of: (A) applying an initial pulse of RF energy to the tissue, the pulse having characteristics selected so as not to excessively heat the tissue; (B) measuring at least one electrical characteristic of the tissue in response to the applied pulse; (C) in accordance with the measured electrical characteristic, determining an initial set of pulse parameters for use during a first RF energy pulse that is applied to the tissue; and (D) varying the pulse parameters of individual ones of subsequent RF energy pulses in accordance with at least one characteristic of an electric current transient that occurs at the beginning of each individual one (pulses) of the subsequent RF energy pulses.

The method can terminate the generation of subsequent RF energy pulses upon a determination that the current transient is absent or that the voltage has been reduced to a predefined level. In another embodiment of the present invention, the initial pulse may be combined with at least the first subsequent pulse.

Figure 10:
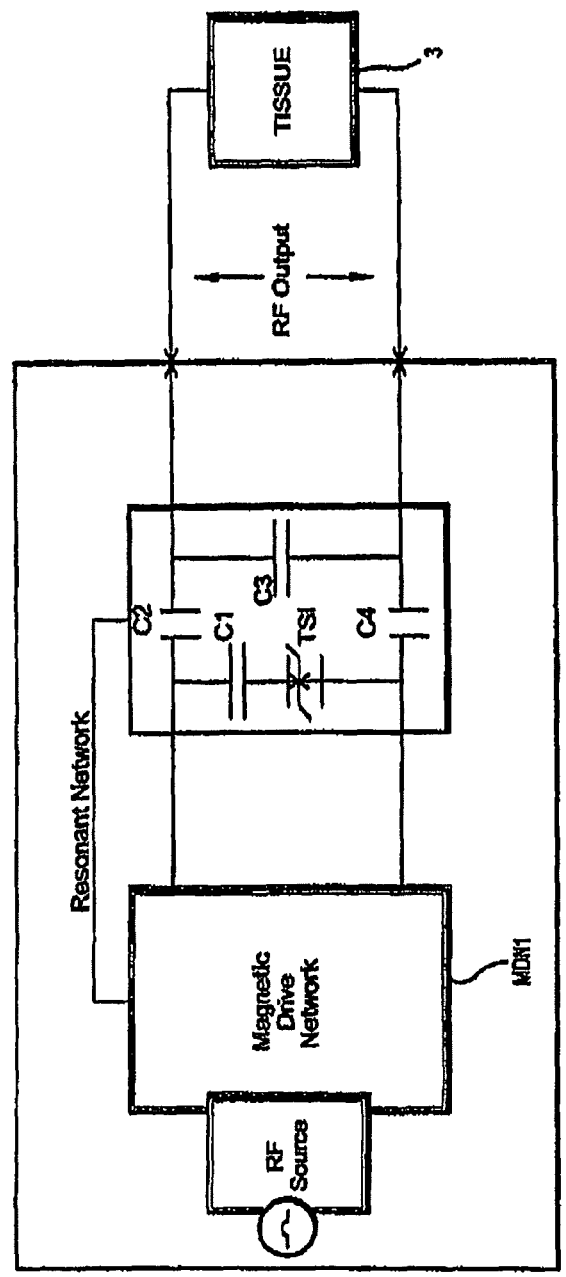
FIG. 10 is a simplified block diagram of a circuit for achieving an overvoltage limiting and transient energy suppression energy function.
Figure 11:
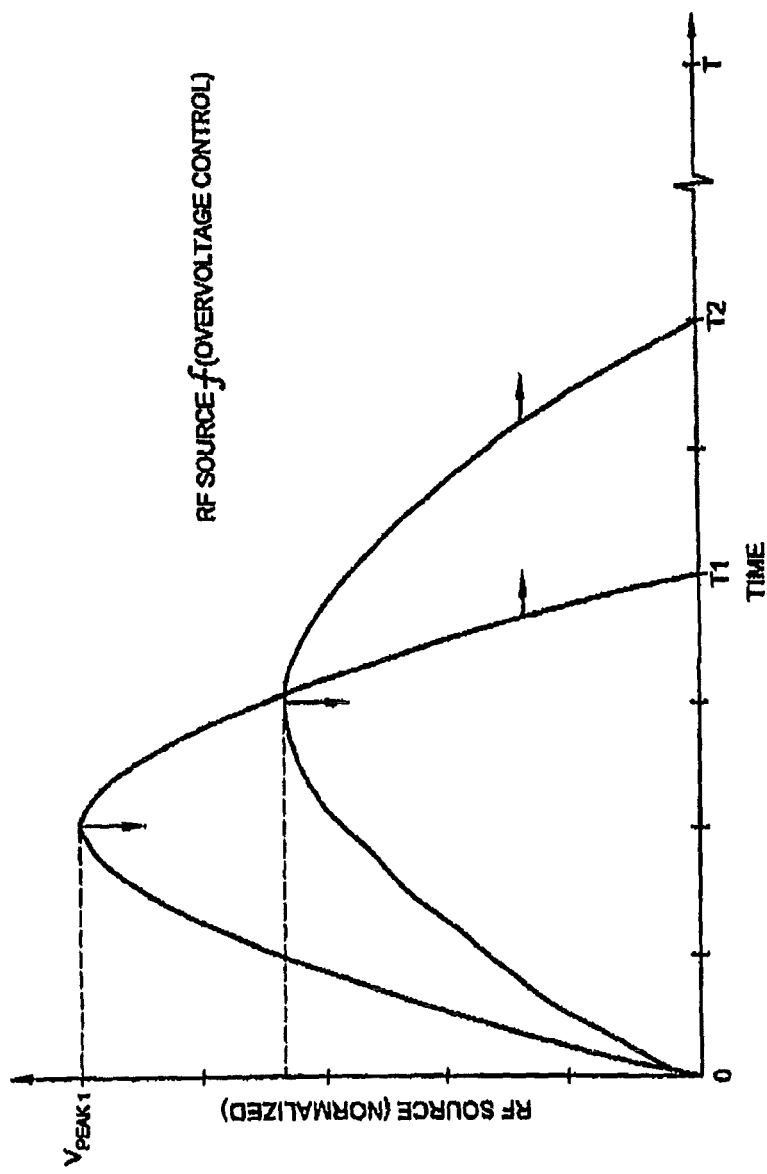
FIG. 11 is a waveform diagram illustrating the effect of the operation of the circuit in FIG. 10.

Reference is now made to FIGS. 10 and 11 for a description of a novel overvoltage limit and transient energy suppression aspect of the system disclosed herein.

A bi-directional transorb TS1 normally is non-operational. As long as the operating RF output levels stay below the turn-on threshold of TS1, electrosurgical energy is provided at a controlled rate of tissue desiccation. However, in the event that rapid tissue desiccation occurs, or that arcing is present in the surgical tissue field, the RF output may exhibit operating voltage levels in excess of the normal RF levels used to achieve the controlled rate of tissue desiccation. If the excess voltage present is left unrestrained, the tissue 3 may begin to exhibit undesirable clinical effects contrary to the desired clinical outcome. The TS1 is a strategic threshold that is set to turn on above normal operating levels, but below and just prior to the RF output reaching an excess voltage level where undesirable tissue effects begin to occur. The voltage applied across TS1 is proportionately scaled to follow the RF output voltage delivered to the tissue 3. The transorb TS1 is selected such that its turn on response is faster than the generator source RF signal. This allows the transorb TS1 to automatically track and respond quickly in the first cycle of an excess RF output overvoltage condition.

Note should be made in FIG. 10 of the capacitor components or network C2, C3, and C4 that parallel the magnetic drive network (MDN1) which has an inductive characteristic and is contained within the electrosurgical generator 2. The combination of the inductive MDN1 and the capacitive networks forms a resonant tuned network which yields the waveshape configuration of the RF source signal shown in FIG. 11.

A turn on of transorb device TS1, which functions as a voltage controlled switch, instantaneously connects the serial capacitance C1 across the capacitor network C2, C3, and C4. An immediate change then appears in the tuning of the resonant network mentioned above, which then instantaneously alters the waveshape of the RF source signal shown in FIG. 11. The time base T1 of the nominally half-sine signal shown increases incrementally in width out to time T2, which automatically lowers the peak voltage of the RF output signal. The peak voltage decreases because the Voltage-Time product of the signal shown in FIG. 11 is constant for a given operating quiescence. The concept of a Voltage-Time product is well known to those skilled in the art, and is not further discussed herein.

As the peak voltage decreases, the excess overvoltage is automatically limited and is restricted to operating levels below that which cause negative clinical effects. Once the excess RF output voltage level falls below the transorb threshold, the TS1 device turns off and the electrosurgical generator 2 returns to a controlled rate of tissue desiccation.

In the event that arcing is present in the surgical tissue field, undesirable excess transient RF energy may exist and may be reflected in the RF output of the electrosurgical generator 2. This in turn may generate a corresponding excess RF output voltage that creates sufficient transient overvoltage to turn on the transorb TS1. In this condition the cycle repeats as described above, where TS1 turns on, alters the resonant tuned network comprised of the magnetic and capacitive components, and thus also alters the RF source signal waveshape. This automatically reduces the excess overvoltage.

In accordance with this aspect of the disclosure, the excess RF transient energy is suppressed and the overvoltage is limited by the dynamic, real-time automatic detuning of the RF energy delivered to the tissue being treated.

It should be noted that the embodiment of FIGS. 10 and 11 can be used to improve the operation of conventional electrosurgical generators, as well as with the novel pulsed output electrosurgical generator 2 that was described previously.

Figure 14:
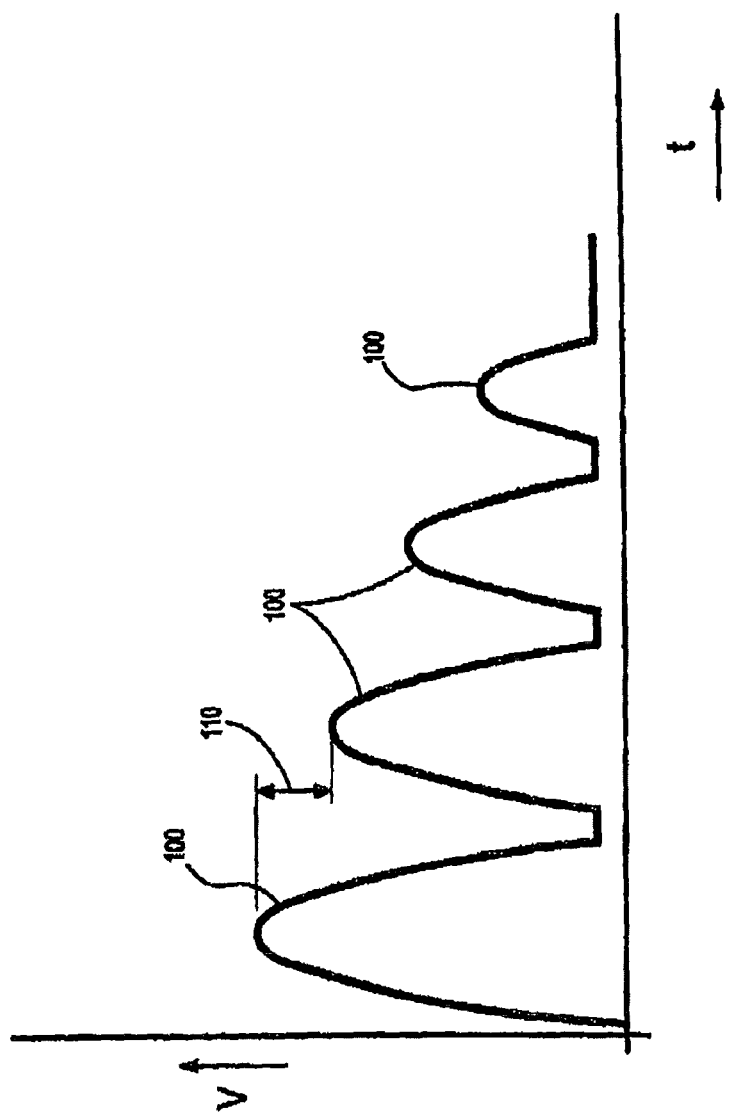
FIG. 14 is a chart illustrating a fixed number of pulses determined from the measured impedance and the RMS current pulse width.

In an additional embodiment the measured electrical characteristic of the tissue, preferably the impedance ($Z_i$), and the RMS current pulse width ($P_W$) may be used to determine a fixed voltage reduction factor ($V_{dec}$) to be used for subsequent pulses, and to determine a fixed number of pulses ($P_F$) to be delivered for the sealing procedure. The relationship among the voltage reduction factor, the measured impedance and the RMS current pulse width may be defined as $V_{dec}$=F ($Z_I$, $P_W$), and the relationship among the number of pulses, the measured impedance and the RMS current pulse width may be defined as $P_F$=F' ($Z_I$, $P_W$). In FIG. 14 a fixed number of pulses, $P_F$, 100 determined from the measured impedance and the RMS current pulse width are shown. Each subsequent pulse may be reduced by the fixed voltage reduction factor ($V_{dec}$) 110, also determined from the measured impedance and the RMS current pulse width.

In a further additional embodiment, tissue sealing is accomplished by the electrosurgical system described above by continuously monitoring or sensing the current or tissue impedance rate of change. If the rate of change increases above a predetermined limit, then RF pulsing is automatically terminated by controlling the electrosurgical generator 2 accordingly and any previously changed pulse parameters (e.g., power, voltage and current increments) are reset to the original default values. In this embodiment, the ending current or tissue impedance, i.e., the current or tissue impedance at the end of each RF pulse, is also continuously monitored or sensed. The ending values are then used to determine the pulse parameters for the subsequent RF pulse; to determine if the seal cycle should end (based on the ending values of the last few RF pulses which did not change by more than a predetermined amount); and to determine the duty cycle of the subsequent RF pulse.

Further, in this embodiment, RF power, pulse width, current and/or voltage levels of subsequent RF pulses can be kept constant or modified on a pulse-by-pulse basis depending on whether the tissue has responded to the previously applied RF energy or pulse (i.e., if the tissue impedance has begun to rise). For example, if the tissue has not responded to a previously applied RF pulse, the RF power output, pulse width, current and/or voltage levels are increased for the subsequent RF pulse.

Hence, since these RF pulse parameters can subsequently be modified following the initial RF pulse, the initial set of RF pulse parameters, i.e., a magnitude of a starting RF power level, a magnitude of a starting voltage level, a magnitude of the starting pulse width, and a magnitude of a starting current level, are selected accordingly such that the first or initial RF pulse does not excessively heat the tissue. One or more of these starting levels are modified during subsequent RF pulses to account for varying tissue properties, if the tissue has not responded to the previously applied RF pulse which includes the initial RF pulse.

The above functions are implemented by a seal intensity algorithm represented as a set of programmable instructions configured for being executed by at least one processing unit of a vessel sealing system. The vessel sealing system includes a Seal Intensity control panel for manually adjusting the starting voltage level, in a similar fashion as described above with reference to FIGS. 9A and 9B.

Figure 15:
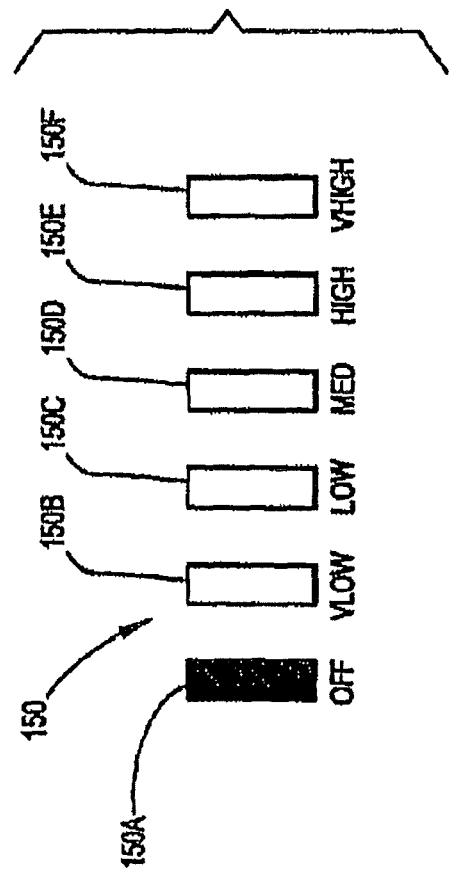
FIG. 15 illustrates a Seal Intensity control that forms a part of this disclosure.

As shown in FIG. 15, a preferred Seal Intensity control panel of the present inventive embodiment includes six settings, i.e., "Off" 150A, "VLOW" 150B, "LOW" 150C, "MED" 150D, "HIGH" 150E and "VHIGH" 150F. The Seal Intensity front panel settings 150 adjust the seal parameter values of the Seal Parameter Table as shown by FIGS. 9B and 9C. The selected Seal Parameter Table, adjusted by the Seal Intensity front panel settings 150 is then utilized by an RF generation system, as described above, and an initial RF sealing pulse is then started.

The Seal Intensity front panel settings, as shown in FIGS. 9B and 9C, represent approximate parametric values of several preferred embodiments, identified as an example to achieve vessel sealing performance in clinical procedures. The variety of tissue types and surgical procedures requires the use of one or more Seal Intensity front panel settings.

Figure 16:
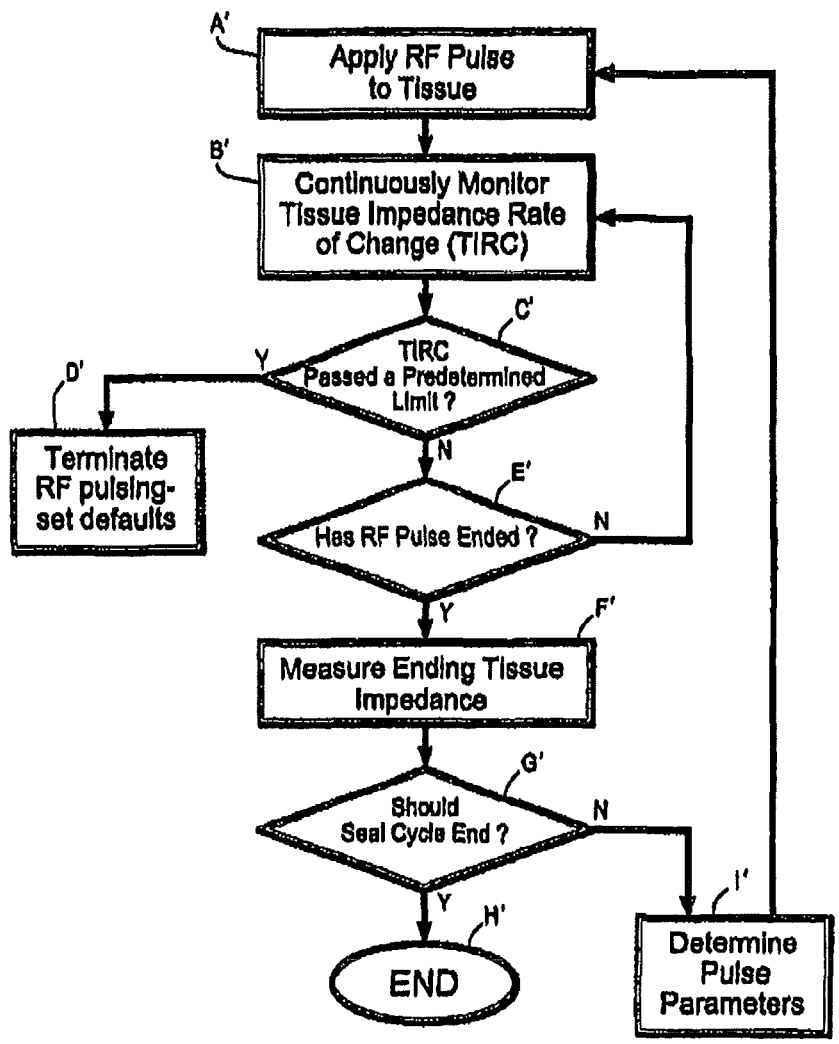
FIG. 16 is a logic flow diagram that illustrates another method in accordance with the system disclosed herein.

FIG. 16 is a logic flow diagram that illustrates a method in accordance with the vessel sealing system. At step A', a RF pulse is applied to tissue. At step B', the current or tissue impedance rate of change is continuously monitored. At step C', a determination is made whether the tissue impedance rate of change has passed a predetermined limit. If yes, at step D', RF pulsing is terminated and any previously changed pulse parameters are reset back to the original defaults. If no, the process proceeds to step E'.

At step E', a determination is made as to whether the RF pulse has ended. If no, the process loops back to step B'. If yes, the process proceeds to step F'. At step F', the ending current or tissue impedance is measured. At step G', the measured ending values are used for determining if the seal cycle should end (based on the current level or ending impedance of the last few RF pulses which did not change by more than a predetermined amount). If yes, the process terminates at step H'. If no, the process continues at step I', where the ending values are used for determining the pulse parameters, i.e., the power, pulse width, current and/or voltage levels, and the duty cycle of the subsequent RF pulse from an entry in one of a plurality of lookup tables. The process then loops back to step A'. One of the plurality of lookup tables is selected manually or automatically, based on a choice of an electrosurgical tool or instrument.

While the system has been particularly shown and described with respect to preferred embodiments thereof, it will be understood by those skilled in the art that changes in form and details may be made therein without departing from its scope and spirit.

What is claimed is:

1. A system for electrosurgically sealing tissue, comprising:
   a surgical instrument adapted to position a first electrode and a second electrode about tissue forming a gap therebetween; and
   an electrosurgical generator electrically coupled to the first and second electrodes of the surgical instrument and adapted supply RF energy to the first and second electrodes, wherein the electrosurgical generator supplies a first pulse of RF energy to the first and second electrodes forming a first electrical potential therebetween and at least one subsequent pulse of RF energy to the first and second electrodes forming at least one subsequent electrical potential therebetween,
   wherein the electrosurgical generator is configured to regulate the at least one subsequent pulse of RF energy to decrease the subsequent electrical potential as the gap between the first and second electrodes is decreased.

2. The system according to claim 1, wherein an amplitude of one of the at least one subsequent pulses is decreased to compensate for thermally-induced shrinkage of tissue.

3. The system according to claim 1, wherein the electrosurgical generator is configured to supply a plurality of subsequent pulses of RF energy to the first and second electrodes while controllably decreasing an amplitude of each individual one of the plurality of subsequent pulses of RF energy.

4. The system in according to claim 1, wherein the electrosurgical generator is configured to controllably decrease an amplitude of one of the at least one subsequent pulses of RF energy to compensate for a decrease in the gap between the first and second electrodes.

5. A system for electrosurgically sealing tissue, comprising:
 a surgical instrument adapted to position a first electrode and a second electrode about tissue forming a gap therebetween; and
 an electrosurgical generator, electrically coupled to the first and second electrodes of the surgical instrument, the electrosurgical generator including:
  a controller configured to apply a first pulse of RF energy to the first and second electrodes forming an electrical potential therebetween and the controller configured to apply at least one subsequent pulse of RF energy to the first and second electrodes forming a subsequent electrical potential therebetween;
  wherein the controller regulates the at least one subsequent pulse of RF energy to decreases the subsequent electrical potential as the gap between the first and second electrodes is decreased.

6. The system according to claim 5, wherein the controller decreases an amplitude of one of the at least one subsequent pulses of RF energy to compensate for thermally-induced shrinkage of the tissue.

7. The system according to claim 5, wherein the controller applies a plurality of subsequent pulses of RF energy to the first and second electrodes while controllably decreasing an amplitude of each individual one of the plurality of subsequent pulses of RF energy.

8. The system according to claim 5, wherein an amplitude of one of the at least one subsequent pulses of RF energy is controllably decreased to compensate for a decrease in gap between the first and second electrodes due to a thermally-induced shrinkage of tissue.

9. The system according to claim 5, wherein the controller decreases an amplitude of one of the at least one subsequent pulses of RF energy to compensate for a decrease in the gap between the first and second electrode.

* * * * *